United States Patent [19]

Hamma et al.

[11] Patent Number: 5,030,626
[45] Date of Patent: Jul. 9, 1991

[54] FLUORINE DERIVATIVES OF VITAMIN $D_3$ AND PROCESS FOR PRODUCING THE SAME

[75] Inventors: Noritaka Hamma, Sakai; Yoshikazu Saito, Nishinomiya; Toshio Nishizawa, Suita; Takashi Katsumata; Itsuro Sugata, both of Toyonaka, all of Japan

[73] Assignees: Sumitomo Pharmaceuticals Company, Limited, Osaka; Taisho Pharmaceutical Co., Ltd., Tokyo, both of Japan

[21] Appl. No.: 512,560

[22] Filed: Apr. 24, 1990

Related U.S. Application Data

[63] Continuation of Ser. No. 39,953, Apr. 20, 1987, abandoned.

[30] Foreign Application Priority Data

Apr. 25, 1986 [JP] Japan ................................. 61-94596
Apr. 10, 1987 [JP] Japan ................................. 62-88126

[51] Int. Cl.[5] ............................................. A01N 45/00
[52] U.S. Cl. .................................... 514/167; 552/502; 514/825
[58] Field of Search ......................... 514/167; 552/502

[56] References Cited

U.S. PATENT DOCUMENTS

| | | | |
|---|---|---|---|
| 4,248,791 | 2/1981 | De Luca | 552/546 |
| 4,358,406 | 11/1982 | De Luca | 540/78 |
| 4,411,833 | 10/1983 | DeLuca et al. | 260/397.2 |
| 4,495,181 | 1/1985 | Norman et al. | 514/167 |
| 4,521,410 | 6/1985 | Holick et al. | 514/169 |
| 4,594,432 | 6/1986 | Baggiolini et al. | 260/397.2 |

FOREIGN PATENT DOCUMENTS

81/02298 8/1981 World Int. Prop. O. .

OTHER PUBLICATIONS

Chemical Abstracts, vol. 106, No. 19, May 11, 1987, p. 4, ref. no. 156774y.
Chemical Abstracts, vol. 106, No. 11, Mar. 16, 1987, p. 643, ref no. 84955h.
Proceeding of the National Academy of Sciences, vol. 80, Jan. 1983, pp. 201-204.
Chemical Abstracts, vol. 102, No. 1, Jan. 1985; p. 549, Abstract No. 6060r.
Chemical Abstracts, vol. 103, No. 15, Oct. 1985, p. 83, Abstract No. 116282t.
Chemical Abstracts, vol. 104, No. 20, May 1986, p. 391, Abstract No. 174664a.
J. Biol. Chem., 248, 6691-6695 (1973).
Biochemistry 23, 3973-3979 (1984).
Archives of Biochemistry and Biophysics, vol. 229, No. 1, (1984), pp. 348-354.
*Biological Activity Assessment of the Vitamin D Metabolites*, Mayer et al., Archives of Biochemistry and Physics, vol. 224 (1983), pp. 671-676.
Studies on Organic Fluorine Compounds. XXXIX, Kobayashi et al., Chem. Pharm. Bull., vol. 30 (1982), pp. 4297-4303.

*Primary Examiner*—Stanley J. Friedman
*Assistant Examiner*—Theodore J. Criares
*Attorney, Agent, or Firm*—Stevens, Davis, Miller & Mosher

[57] ABSTRACT

There are disclosed herein novel derivatives of 26,26,26,27,27,27-hexafluorovitamin $D_3$ providing excellent pharmacological effects, and a process for the preparation thereof. These novel compounds are represented by the general formula wherein $R_1$ and $R_2$ each denotes a hydrogen atom or a protecting group for the hydroxyl group; $R_3$ and $R_4$ each denotes a hydrogen atom, a hydroxyl group or a protected hydroxyl group and $R_4'$ and $R_5'$ each denotes a hydrogen atom, or alternatively $R_3$ and $R_3'$ together or $R_4$ and $R_4'$ together denote an oxo group; provided that $R_3$, $R_3'$, $R_4$ and $R_4'$ cannot denote hydrogen atoms simultaneously. The process for the preparation comprises subjecting a previtamin $D_3$ derivative represented by the formula wherein $R_1$, $R_2$, $R_3$, $R_3'$, $R_4$ and $R_4'$ are as defined above, to thermal isomerization to give a vitamin $D_3$ derivative represented by the general formula (Abstract continued on next page.)

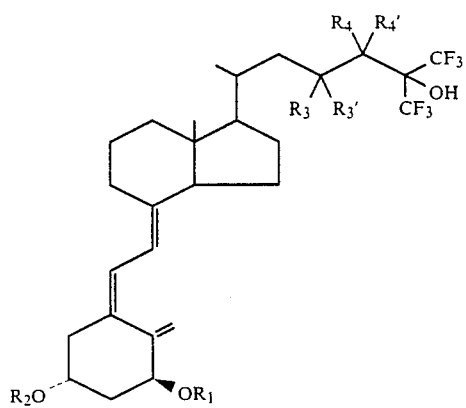
wherein $R_1$, $R_2$, $R_3$, $R_3'$, $R_4$ and $R_4'$ are as defined above, and optionally subjecting it to a deprotection reaction.
21 Claims, No Drawings

FLUORINE DERIVATIVES OF VITAMIN $D_3$ AND PROCESS FOR PRODUCING THE SAME

This application is a continuation of application Ser. No. 07/039,953, filed Apr. 20, 1987, now abandoned.

BACKGROUND AND TECHNICAL FIELD OF THE INVENTION

This invention relates to a novel fluorine derivative of vitamin $D_3$. More particularly, it relates to a novel fluorine drivative of vitamine $D_3$ which not only has an excellent pharmacological activity, namely a useful vitamine D-like physiological activity, and is useful as a curative or preventive medicine for various diseases caused by disorders of absorption, transportation or metabolism of calcium, for example bone diseases such as rickets, osteomalacia and osteoporosis, but also has an ability to suppress the proliferation of tumor cells such as myeloleukemia cells and induce the differentiation of these cells into normal cells, is thus useful as an antitumor agent and additionally can manifest its effect for many hours. Further, the compound of this invention is useful also as a curative medicine for rheumatism and psoriasis.

PRIOR ART

It is known that 1α,25-dihydroxyvitamin $D_3$, which is a metabolite of vitamin $D_3$ in a living body and is known as the active-form of vitamin $D_3$, and its artificial homologues, 1α-hydroxyvitamin $D_3$, 1α,24-dihydroxyvitamin $D_3$ and the like, exhibit an action of stimulating the absorption of calcium from the intestine and are effective as curatives for bone diseases and the like. Further, there has been found recently in vitamin $D_3$ and its analogous compounds a differentiation-inducing action to restore cancerated cells into normal cells (Hirobumi Tanaka et al., The Journal of Japanese Biochem. Soc., 55, 1323 (1983)). Actually, some of these compounds have been found to have an antitumor activity (Y. Honma et al., Proc. Natl. Acad. Sci., U.S.A., 80, 201 (1983)) and are attracting attention. However, the results obtained so far are still unsatisfactory.

On the other hand, among the derivatives of vitamin $D_3$ fluorinated at the 26- and the 27-position, 26,26,26,27,27,27-hexafluoro-25-hydroxyvitamin $D_3$ (U.S. Pat. No. 4,248,791) and 26,26,26,27,27,27-hexafluoro-1α,25-dihydroxyvitamin $D_3$ (Japanese National Publication (Kohyo) No. 501,176/83) are known to have a high, vitamin D-like physiological activity, and their effectiveness as an antitumor agent is disclosed in Japanese Patent Application Kokai (Laid-open) No. 7,215/86.

Further, a method for preparing 26,26,26,27,27,27-hexafluoro-25-hydroxy-24-oxovitamin $D_3$ is disclosed in Abstracts of lectures, 105-th Anual Meeting of Pharmaceutical Society Japan (published by Pharmaceutical Society of Japan, March, 1985).

On the other hand, it is known that the vitamin D-like physiological activity is markedly decreased in compounds resulting from the oxidation of the active-form of vitamin $D_3$ at the 23- and/or 24-position, for example 1α,24,25-trihydroxyvitamin $D_3$ and the like, as compared with 1α,25-dihydroxyvitamin $D_3$, which is the active form. (J. Biol. Chem., 248, 6691 (1973)).

SUMMARY OF THE INVENTION

The object of this invention is to provide a 26,26,26,27,27,27-hexafluorovitamin $D_3$ derivative which is a novel compound and has an excellent pharmacological activity.

DETAILED DESCRIPTION OF THE INVENTION

The fluorine-containing vitamin $D_3$ derivative provided according to this invention is represented by the general formula [1]

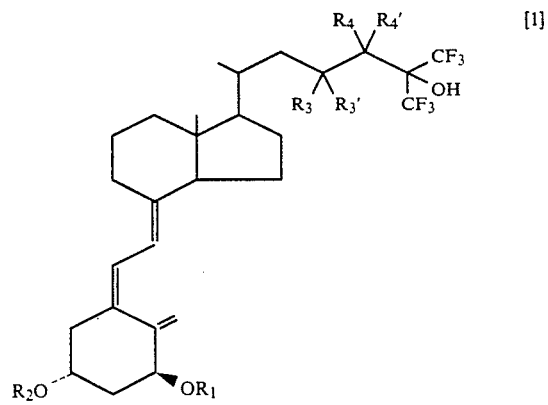

wherein $R_1$ and $R_2$ each denotes a hydrogen atom or a protecting group for the hydroxyl group; $R_3$ and $R_4$ each denotes a hydrogen atom, a hydroxyl group or a protected hydroxyl group and $R_3'$ and $R_4'$ each denotes a hydrogen atom, or alternatively $R_3$ and $R_3'$ together or $R_4$ and $R_4'$ together denote an oxo group; provided that $R_3$, $R_3'$, $R_4$ and $R_4'$ cannot denote hydrogen atoms simultaneously. When $R_3$ or $R_4$ in the above general formula [1] is a hydroxyl group, there exist diastereomers resulting from the presence of the asymmetric carbon atoms at the 23- and/or the 24-position. This invention includes all of these diastereomers.

Compounds obtained by eliminating all of the protecting groups for the hydroxyl group from the compound of the general formula [1], namely compounds represented by the general formula [1']

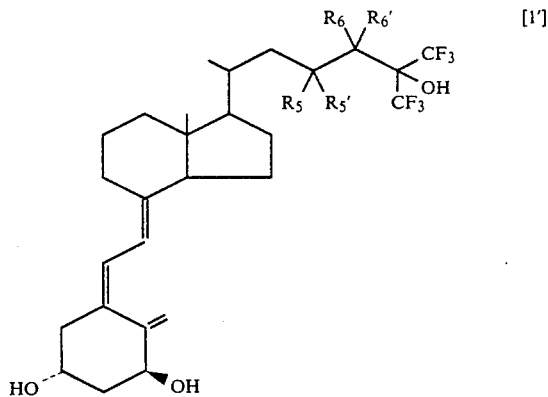

wherein $R_5$ and $R_6$ each denotes a hydrogen atom or a hydroxyl group and $R_5'$ and $R_6'$ each denotes a hydrogen atoms, or alternatively $R_5$ and $R_5'$ together or $R_6$ and $R_6'$ denote an oxo group, provided that $R_5$, $R_5'$, $R_6$ and $R_6'$ cannot denote hydrogen atoms simultaneously, exhibit a vitamin D-like action and is hence useful as a curative or preventive medium for bone diseases; further they exhibit a cell differentiation-inducing action and are hence useful as a cell-differentiation inducing agent or an antitumor agent, and are also useful as an antirheumatic agent or for the treatment of cutaneous diseases such as psoriasis.

Further, compounds wherein, in the above-mentioned formula [1], $R_1$ or $R_2$ is a protecting group for the hydroxyl group; or $R_3$ or $R_4$ is a protected hydroxyl group, are useful as an intermediate for producing the compound represented by the general formula [1'] mentioned above.

It was utterly unanticipated that the compound represented by the general formula [1'] mentioned above might exhibit a powerful vitamin D-like activity inspite of its having a hydroxyl group or oxo group at the 23- and/or the 24-position. These compounds of this invention can be expected particularly as a vitamin D-like medicine of low toxicity.

The compound of the formula [1] of this invention can be prepared by various method known to the art as the method of preparing vitamin $D_3$ and its analogues. For example, it can be prepared easily and yet advantageously by the method shown by the following reaction scheme.

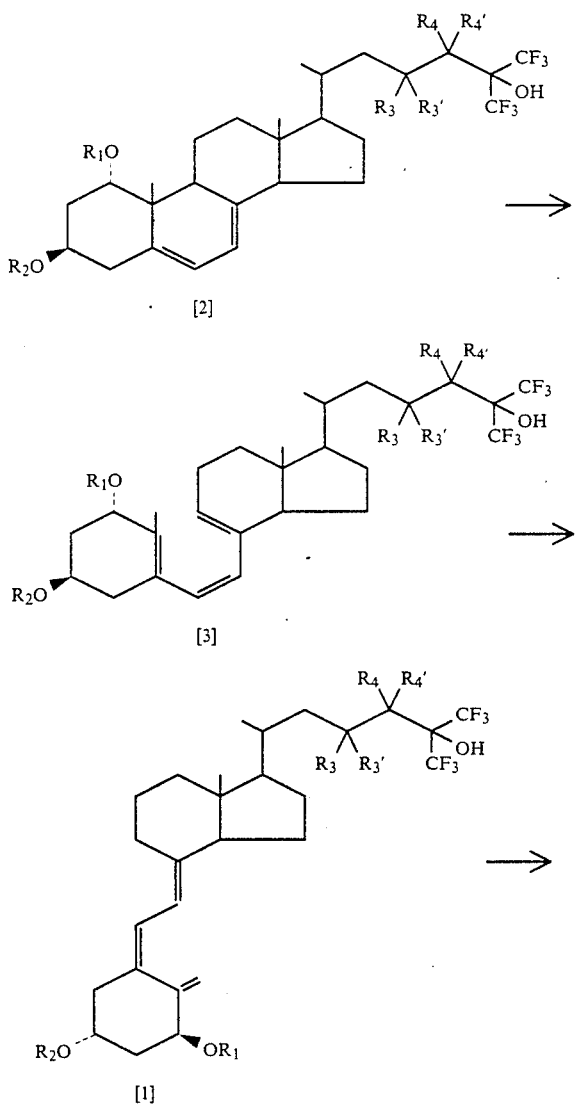

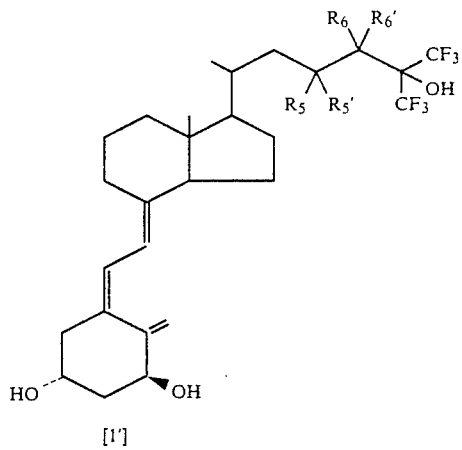

In the above-shown reaction scheme, $R_1$, $R_2$, $R_3$, $R_4$, $R_4'$, $R_5$, $R_5'$, $R_6$ and $R_6'$ have the same meaning as mentioned before. The term "protecting group" referred to herein means a group which is generally used in the art as a protecting group for the hydroxyl group and which can be easily eliminated as occasion demands by conventional means such as acids, bases, or reduction. As examples of the protecting groups included in this invention, mention may be made of acyl groups such as alkanoyl groups and aromatic acyl groups; ethereal protecting group, aralkyl groups, lower alkylsilyl groups, and lower alkoxycarbonyl groups. As more specific examples, there may be mentioned: for alkanoyl groups, lower alkanoyl groups of 2 to 5 carbon atoms such as acetyl, propionyl and pivaloyl; for aromatic acyl groups, an optionally substituted benzoyl group such as benzoyl and p-chlorobenzoyl; for ethereal protective groups, methoxymethyl, 2-methoxyethyl, and 2-tetrahydropyranyl; for aralkyl groups, an optionally substituted benzyl group such as benzyl and p-nitrobenzyl; for lower alkylsilyl groups, trialkylsilyl groups having alkyl groups of 1 to 4 carbon atoms such as trimethylsilyl; and for lower alkoxycarbonyl groups, alkoxycarbonyl groups whose alkoxy moiety has 1 to 4 carbon atoms, such as methoxycarbonyl and ethoxycarbonyl. Among these protecting groups, particularly acyl groups such as acetyl and benzoyl are advantageously used.

Now, procedures for executing the respective reaction steps of the reaction scheme shown above will be described in detail below.

The step for the compound [3] is carried out by a method known per se, namely by irradiating the compound [2] with ultraviolet light. The step of ultraviolet irradiation is carried out by irradiating a compound represented by the general formula [2] with ultraviolet light in a suitable inert solvent, for example organic solvents such as benzene, toluene, n-hexane, methanol, ethanol, diethyl ether and acetonitrile or the mixture thereof and in an atmosphere of inert gas such as nitrogen and argon. The source of ultraviolet light may be those conventionally used, including, for example, a mercury lamp as an easily available one. A filter may be used together according to necessity. An irradiation temperature of $-10°$ to $40°$ C., preferably $-10°$ to $20°$ C., gives good results. Although the irradiation time varies depending on the kind of ultraviolet source, the concentration of the starting compound of the formula

[2] and the kind of solvent, it is usually several to several tens of minutes. Although the compound of the formula [3] formed by the ultraviolet irradiation may be isolated by simple means such as chromatography, usually it is more common to carry out thermal isomerization by heating the reaction liquid without isolating the compound after the completion of the ultraviolet-irradiated reaction, thus to follow the reaction scheme continually up to the step for the compound [1].

The reaction step for the compound [1] is also carried out by a method known per se. Thus, it is conducted by heating the compound [3] in a suitable inert solvent, preferably the solvent used in the above-mentioned ultraviolet irradiation step, at 20° to 120° C., preferably 50° to 100° C., for 2 to 5 hours. The reaction is preferably carried out in an inert gas such as nitrogen or argon. The isolation of the compound [1] from the reaction mixture is effected, after the solvent has been distilled off, by simple means such as chromatography.

When the compound of the formula [1] thus obtained has the above-mentioned protecting group, it is subjected to a deprotection reaction to obtain the final objective compound of the formula [1'] of this invention. The deprotection reaction may be effected by a method known per se adopted depending on the kind of protecting group mentioned above.

Thus, the compound of the formula [1] of this invention is obtained.

The compound of the formula [2] used as the starting material in the above-mentioned reaction is also a novel compound. Although the compound may be prepared by various methods, it is advantageously obtained, for example, by using the following method found by the present invention.

First, a compound of the formula [1] wherein $R_3$ and $R_3'$ are each a hydrogen atom, namely a compound represented by the general formula [5]

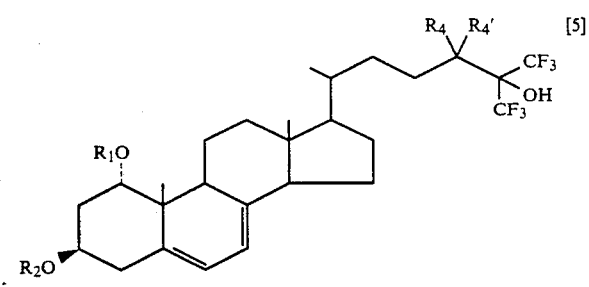

wherein $R_1$, $R_2$, and $R_4'$ are as defined above, can be easily obtained by the method shown by the following reaction scheme.

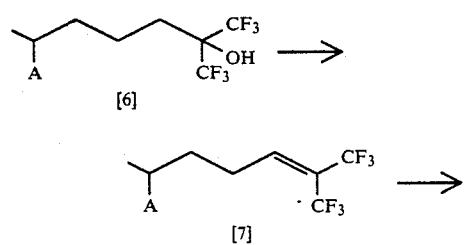

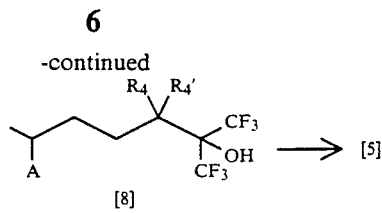

In the above reaction scheme, $R_4$ and $R_4'$ are as defined above, and A denotes a steroid residue represented by the general formula [4]

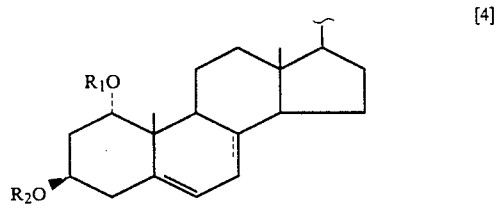

wherein $R_1$ and $R_2$ are as defined above and the dotted line ..... between the carbon atoms of the 7- and the 8-position signifies the optional presence of a bond.

First, a fluorine derivative of 25-hydroxycholesterol represented by the general formula [6] is treated with a dehydrating agent to give a 24-dehydro compound represented by the general formula [7]. The dehydrating agent used herein is an agent generally used for halogenation of the hydroxyl group, such as thionyl chloride, phosphorus trichloride, phosphorus tribromide, methanesulfonyl chloride, acetyl chloride, and tri-substituted phosphine-carbon tetrahalide. Particularly, tri-substituted phosphine-carbon tetrahalide systems, such as triphenylphosphine-carbon tetrachloride and trioctylphosphine-carbon tetrachloride, give good results. As an example of procedures for executing the present invention, the dehydration of the compound of the formula [6] by means of triphenylphosphine-carbon tetrachloride will be described in detail below. First, triphenylphosphine and carbon tetrachloride are added to the compound of the formula [6] and the mixture is allowed to react at from room temperature to about 100° C. Although a solvent is not necessarily needed in the reaction, an inert organic solvent may also be used. As to the amount of triphenylphosphine and carbon tetrachloride, good results are obtained when they are used respectively in an equimolar amount or more, preferably 1 to 5 molar amount, relative to the starting compound of the formula [6]. The isolation of the objective product of the formula [7] from the reaction mixture can be effected by conventional means such as column chromatography or recrystallization. Thus, the compound of the formula [7] is obtained from the compound of the formula [6] in a high yield. The method of preparation of the starting compound of the formula [6] used herein is disclosed in Japanese National Publication (Kohyo) Nos. 501,176/83 and 500,864/84 and J. Chem. Soc., Chem. Commun., 459 (1980).

Although various methods are conceivable to prepare the compound of the formula [8] from the compound of the formula [7] thus obtained, the following method found by the present inventors is simple and advantageous.

Thus, the fluorine derivative of 24-dehydrocholesterol represented by the general formula [7] is treated with a permanganate, whereby only the double bond at the 24-position is oxidized selectively and the intended product of the formula [8] is easily obtained in one step. By selecting reaction conditions properly as described in detail below, it is possible to prepare selectively either a compound of the general formula [8] wherein $R_4$ is a hydroxyl group (24-hydroxy compound) or a compound of said formula wherein $R_4$ and $R_4'$ together denote an oxo group (24-oxo compound).

For preparing the 24-hydroxy compound, the compound of the formula [7] is dissolved or suspended in a suitable inert solvent such as acetone, methyl ethyl ketone, methylene chloride, chloroform, benzene or toluene, and then a permanganate, such as sodium permanganate or potassium permanganate, is added thereto to effect reaction. In this case, the intended 24-hydroxy compound can be selectively prepared by carrying out the reaction under alkaline conditions by adding an inorganic alkali such as sodium hydroxide, potassium hydroxide, sodium carbonate or potassium carbonate. The amount of the permanganate is about 0.5 to 3 molar amount, preferably the formula [7] to obtain good results. The reaction temperature is about $-80°$ to $50°$ C.; usually room temperature or below is preferable. The isolation of the intended compound of the formula [8] from the reaction mixture is usually conducted by extracting it, optionally after removing the manganese dioxide formed by filtration, and then treating it by conventional means such as silica gel column chromatography. Thus, the 24-hydroxy compound is obtained. In this reaction, two kinds of diastereomers are formed which result from the presence of the asymmetric carbon atom of the 24-position. These two kinds of isomers can be separated, if desired, by usual methods of separation and purification, such as column chromatography and recrystallization.

Then, the preparation of the 24-oxo compound can be attained by adding, to the reaction system, an acid in place of the inorganic alkali used in the preparation of the 24-hydroxy compound mentioned above. Preferred examples of the acid used herein are, particularly, carboxylic acids such as formic acid, acetic acid, propionic acid and benzoic acid; usually acetic acid gives satisfactory results. As to the procedures for carrying out the reaction and the means for isolating the objective compound of the formula [8], those described above for the preparation of the 24-hydroxy compound are preferably used.

When the reaction is carried out in the presence of a neutral inorganic salt such as magnesium sulfate or sodium sulfate added to the reaction system without the addition of inorganic alkali or acids mentioned above, a 24-hydroxy compound and a 24-oxo compound are formed simultaneously. These can be separated from each other by a method of separation such as column chromatography.

It is also possible to convert, by known methods, the 24-hydroxy compound obtained by the above-mentioned method into the corresponding 24-oxo compound by oxidation with an oxidizing agent, or the 24-oxo compound into the 24-hydroxy compound by reduction.

The hydroxyl group at the 24-position of the 24-hydroxy compound thus obtained can also be protected, if desired, by the protecting groups mentioned above.

When no bond is present between the carbon atoms of the 7- and the 8-positions in the compound of the formula [8] thus obtained, a bond can be introduced thereto by a method generally used in the art, thereby to convert the compound into a 5,7-diene derivative of the formula [5]. Thus, a compound of the formula [5], which is included in the compound of the formula [2], can be easily obtained by subjecting a compound of the formula [8] having no bond between the carbon atoms of the 7- and 8-position to halogenation at the 7-position with a halogenating agent such as N-bromosuccinic imide or 1,3-dibromohydantoin and then the dehydrohalogenation with a base such as 2,4,6-collidine or tetra-n-butylammonium fluoride.

Nextly, a compound of the general formula [2] having functional groups simultaneously at both of the 23- and the 24-position may be prepared via a compound represented by the general formula [13] as shown by the following reaction scheme.

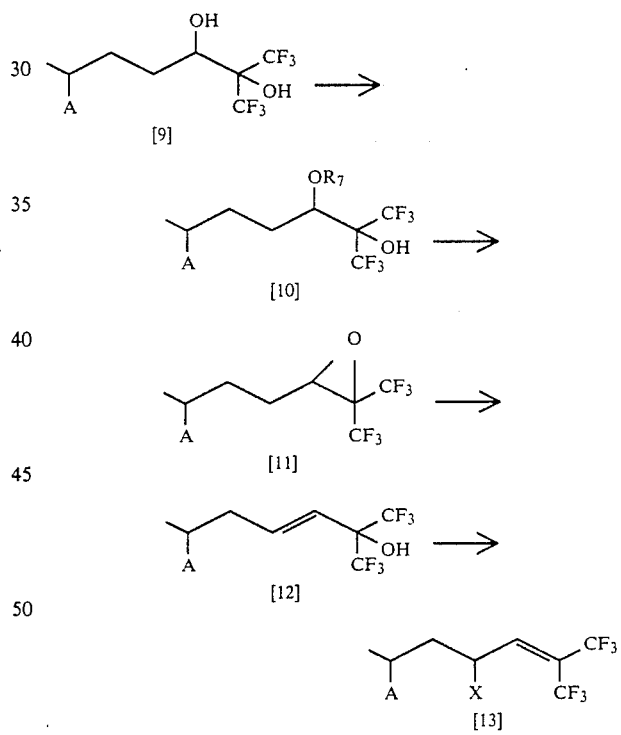

Method 1

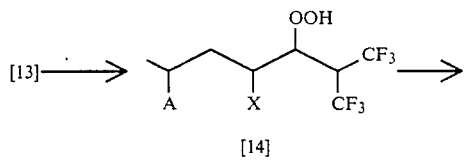

Method 1

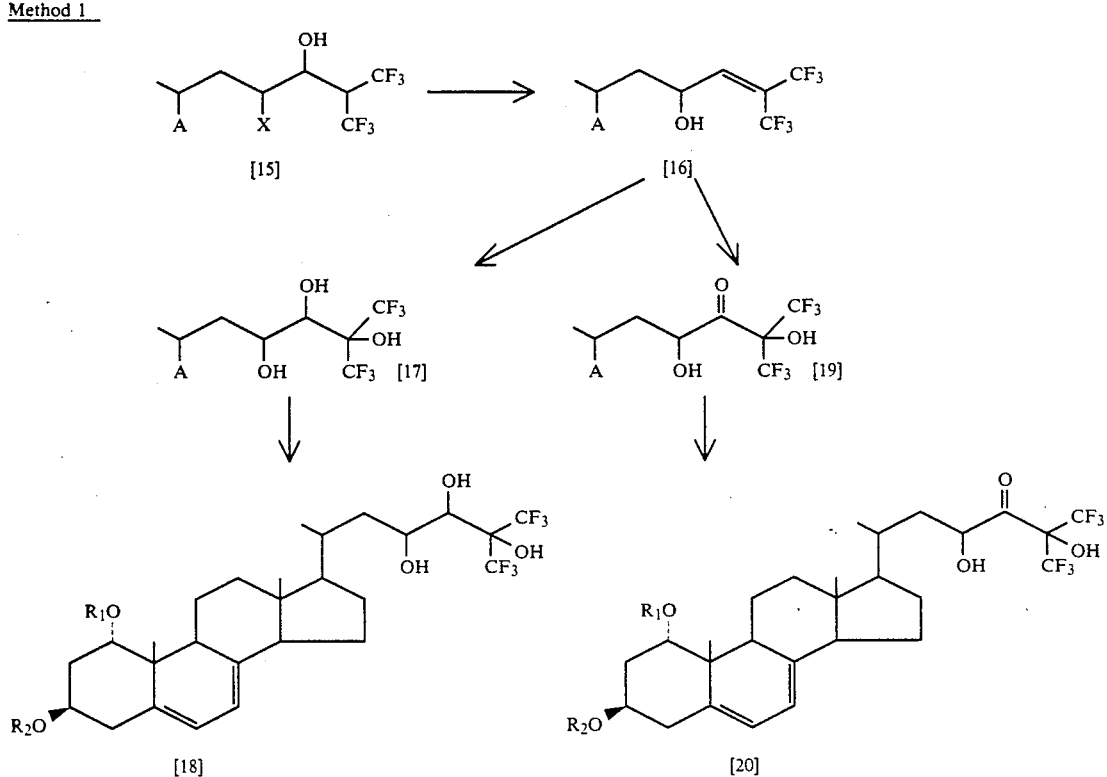

Method 2

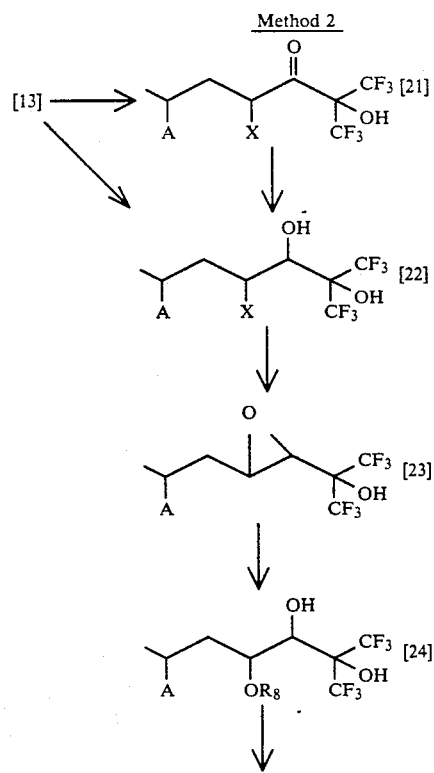

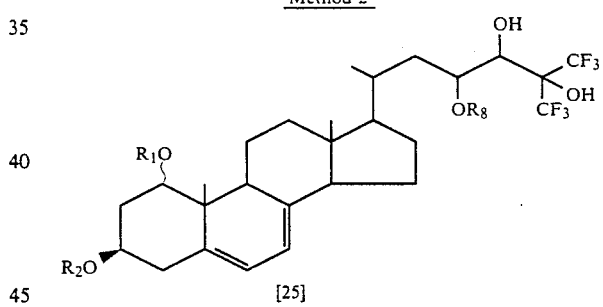

In the reaction scheme shown above, A, $R_1$ and $R_2$ have the same meaning as mentioned before; $R_7$ denotes an alkanesulfonyl or arenesulfonyl group; $R_8$ denotes a hydrogen atom or acyl group; and X denotes a halogen atom, alkanesulfonyloxy group, or arenesulfonyloxy group.

The above-shown method will be further described in detail below. First, the 24-hydroxy compound of the formula [9] obtained by the above-mentioned method is used as the starting material and is sulfonylated by a method known per se to obtain a compound of the formula [10]. Thus, the compound [10] can be easily obtained by reacting the compound [9] with an alkanesulfonyl halide such as methanesulfonyl chloride or an arenesulfonyl halide such as benzenesulfonyl chloride or p-toluenesulfonyl chloride in the presence of a base.

The epoxidation step of the compound [10] can be also conducted by a conventional method of epoxidation. Thus, the compound [10] is treated with a base, for example an inorganic alkali such as sodium hydroxide and potassium hydroxide, a tertiary amine such as triethylamine and tributylamine and a quaternary ammonium salt such as tetra-n-butyl ammonium hydroxide, to give the compound [11] easily. In the case of the compound of this invention, particularly tertiary amines such as triethylamine give good results.

The reaction step for the compound [12] can be also conducted by a method known per se. Thus, the epoxidized compound [11] is dissolved in a suitable inert solvent such as benzene, toluene, diethyl ether, tetrahydrofuran, or dimethylformamide and treated with a base such as potassium t-butoxide, or lithium diisopropylamide to give the compound [12] nearly quantitatively.

The rearrangement reaction from the compound [12] to the compound [13] is effected in the following manner. When X in the general formula [13] is a halogen atom, the rearrangement product [13] wherein X is a halogen atom can be obtained easily and in a high yield by reacting the compound [12] with a halogenating agent. As to the halogenating agent used herein and the procedures for practicing the reaction, those which were described in detail above for the dehydration reaction from the compound [6] to the compound [7] may be used without change. When X is an alkanesulfonyl group such as methanesulfonyl group or an arenesulfonyl group such as benzenesulfonyl group or p-toleuensulfonyl group, the compound [13] can be obtained by reacting the compound [12] with a corresponding alkanesulfonyl halide or arenesulfonyl halide in the presence of a base to obtain a 25-sulfonyloxy compound represented by the general formula

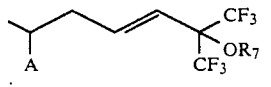

wherein A and $R_7$ are as defined above, and then heating the latter compound at 80° to 200° C., preferably 100° to 150° C., optionally in a suitable inert solvent. The compound [13] obtained by the method of this invention is usually a mixture of two diastereomers resulting from the presence of the asymmetric carbon atom of the 23-position. These diastereomers may also be separated, if desired, by simple means such as recrystallization and column chromatography.

The transformation from the compound [13] thus obtained to the compound [2] having a substituent at the 3- and the 24-position can be carried out by two methods shown below.

Method 1

The reaction step for the compound [14] is carried out by reacting the compound [13] dissolved in a suitable inert solvent with hydrogen peroxide in the presence of a base. As to the solvent used herein, a good result is usually obtained with water, alcohols such as method and ethanol, ethers such as diethyl ether, tetrahydrofuran, and dioxane, amides such as dimethylformamide, or the mixtures thereof. As to bases, inorganic alkalis such as sodium hydroxide, potassium hydroxide, and potassium carbonate are satisfactory. As to their amount to be used, a 0.01 to 0.5 molar amount of the catalyst relative to the compound [13] usually gives a favorable result. Hydrogen peroxide is used in an excessive amount of 5 to 100 moles relative to 1 mole of the compound [13]. A reaction temperature of 0° to 50° C., preferably in the neighborhood of room temperature, gives a good result.

The step for the compound [15] is easily performed by treating the compound [14] by a reduction method generally used for the reduction of hydroperoxides. In the case of the compound of this invention, the most simple method is to reduce the compound [14] with an alkali metal iodide such as potassium iodide and sodium iodide.

The step for the compound [16] is performed by treating the compound [15] with a base. Though both organic and inorganic bases may be used, quaternary ammonium salts give particularly a good result. Thus, a good result is obtained by a method comprising dissolving or suspending the compound [15] in a solvent immiscible with water, such as n-hexane, benzene, toluene, xylene, 1,2-dichloroethane and chloroform, then adding an aqueous solution of caustic alkali, such as sodium hydroxide and potassium hydroxide, and further a quaternary ammonium salt thereto, and allowing the resulting mixture to react in a two-layer system. The quaternary ammonium salts used in this invention include those compounds which are generally used as a phase transfer catalyst. As specific examples thereof, mention may be made of quaternary ammonium halides such as tetra-n-butylammonium chloride and benzyltriethylammonium chloride, and quaternary amine hydroxides such as tetra-n-butylammonium hydroxide. These phase transfer catalysts give a good result at 0.01 to 0.5 molar amount thereof relative to the compound [15]. The reaction is carried out at room temperature to 150° C., but usually at the reflux temperature of the solvent used. The configuration of the 23-position undergoes inversion in the reaction, whereby the compound [16], wherein the 23-position has S-configuration, is obtained from the compound [13] wherein the 23-portion has R-configuration.

The oxidation from the compound [16] to the compound [17] or to the compound [19] can be carried out without difficulty by oxidizing the compound [16] with a permanganate. Thus, the oxidation of the compound [16] with a permanganate gives the compound [17] under basic conditions, and the compound [19] under acidic conditions. The procedures for carrying out the reaction may be those described above for the preparation of the compound [8] from the compound [7] with no change. In this method, the reaction from the compound [16] to the compound [17] proceeds stereoselectively to give the compound [17] wherein the 23- and the 24-position have erytheo configuration. Namely, from the compound [16] wherein the 23-position has S-configuration, is obtained the compound [17] of 23S, 24S.

When the compound [17] and the compound [19] thus obtained have no double bond at the 7,8-position, they can be halogenated at the 7-position and then dehydrohalogenated, as described in detail above for the preparation of the compound [5], to give the compounds [18] and [20], which are included in the compound [2], without difficulty.

Method 2

Compounds included in the compound [2] can be synthesized also by this method.

Transformation from the compound [13] to the compound [22] can be conducted by two kinds of methods. Thus, the oxidation of the compound [13] with a permanganate gives under basic conditions the compound [22] directly, whereas it gives under acidic conditions the compound [21], which gives the compound [22] by reduction. The oxidation with a permanganate can be carried out herein by substantially the same procedures as those described in detail in the preparation of the compound [8] mentioned above. The reduction of the compound [21] is effected by using a reducing agent generally used for reducing a ketone into an alcohol. Usually, sodium borohydride, lithium aluminum hydride, and the like suffice. Though the said two methods each give the compound [22], the resulting compounds [22] differ in the configuration of the 24-position. Thus, transformation from the compound [] 3] directly to the compound [22] gives selectively a compound [22] wherein the configuration at the 23- and the 24-position are in the erythro-form, whereas the method which goes via the 24-oxo compound [21] gives selectively a compound [22] wherein the 24-position has reverse configuration, namely a threo form compound. Accordingly, all of the 4 kinds of diastereomers of the compound [22] resulting from the presence of the asymmetric carbon atoms at the 23- and the 24-position can be prepared by using two isomers consisting of the compounds [13] wherein the 23-position has R- and S-configuration respectively and additionally using the above-mentioned two methods.

The step for the compound [23] can be easily performed by a method generally used in the ring-closing reaction of halohydrins into epoxides, for example by treatment with a base. The base usually used includes inorganic alkali such as sodium hydroxide, potassium hydroxide and sodium carbonate, ammonia, and amines such as triethylamine and tetra-n-butylammonium hydroxide.

The transformation of the compound [23] to the compound [24] by means of a ring-opening reaction can also be carried out by a method known per se. Thus, the compound [23] is allowed to react in water or a solvent mixture of water and an organic solvent and in the presence of an acid such as hydrochloric acid, sulfuric acid, methanesulfonic acid and trifluoromethanesulfonic acid to give the compound [24] wherein $R_8$ is a hydrogen atom. Further, by performing the reaction using acetic acid, propionic acid, isobutyric acid etc. as the solvent and adding the above-mentioned acid to the system, the compound [24] wherein $R_8$ is an acyl group corresponding to the solvent used can be obtained. The configuration at the 23- and the 24-position of the compound [24] thus obtained retains that of the compound When the compound [24] thus obtained has no double bond at the 7,8-position, the compound [24] can be subjected to the 5,7-dienizing reaction by the above-mentioned conventional method to give the compound [25] included in the compound [2].

Further, compounds of the general formula

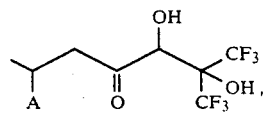

wherein A is as defined above, can be readily obtained by heating the compound [19] in the presence of a tertiary amine such as pyridine or collidine.

Further, compounds of the general formula [2] wherein $R_4$ and $R_4'$ are each a hydrogen atom can be prepared, for example, by the method shown in the following reaction scheme.

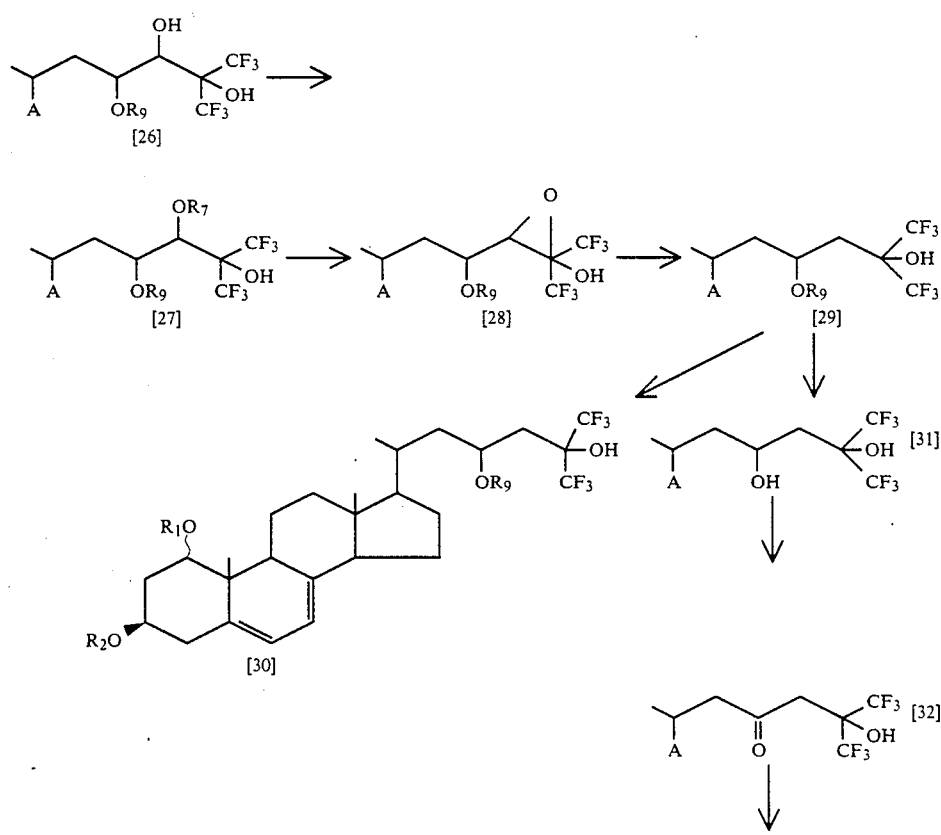

-continued

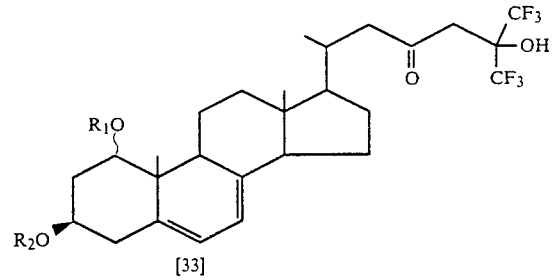

[33]

In the above reaction scheme, A, $R_1$, $R_2$ and $R_7$ are as defined above, and $R_9$ denotes a protecting group for the hydroxyl group. The protecting group for the hydroxyl group denoted by $R_9$ is selected herein from the protecting groups for the hydroxyl group exemplified above. As to the compound [26] used in the reaction, the above-mentioned compound [24] wherein $R_8$ is an acyl group is used as such, or it can be obtained without difficulty either by introducing a protecting group into the compound [17] or by introducing a protecting group into the compound and then oxidizing the resulting product with a permanganate according to the above-mentioned method.

First, the compound [26] is reacted with an alkanesulfonyl halide or arenesulfonyl halide in the same manner as in the preparation of the compound [10] mentioned above, to give the compound [27]. The compound [27] is then treated with a base in the same manner as that shown in the preparation of the compound [11], to give the compound [28] without difficulty.

The step for the compound [29] is performed by a method generally used in the reduction of epoxides. For example, such methods are advantageously used as treatment with a reducing agent such as sodium borohydride and lithium aluminum hydride, or hydrogenation in the presence of a catalyst such as palladium.

When the compound [29] is a 5-ene compound, the compound [30] can be easily obtained by the above-mentioned conventional 5,7-dienizing reaction, namely the bromination of the compound [29] followed by dehydrobromination.

On the other hand, the compound [32] having an oxo group at the 23-position can be obtained by eliminating the protecting group denoted by $R_9$ in the compound [29] to give the compound [31] and then treating the latter with an oxidizing agent. The oxidizing agent used herein may be those generally used in the transformation of the hydroxyl group into the carbonyl group. For the compound of this invention, a good result is obtained with manganese dioxide, chromium trioxide, chromium trioxidepyridine complex, dimethyl sulfoxide-dicyclohexylcarbodiimide, silver nitrate-celite etc.

When the compound [32] thus obtained is a 5-ene compound, it can be subjected to a 5,7-dienizing reaction in the same manner as described above to obtain the compound [33], which is included in the compound [2].

As described in detail above, the compound [2] having a functional group at the 23- or the 23,24-position can be prepared by utilizing the reactions shown below.

Thus, a compound represented by the general formula [34]

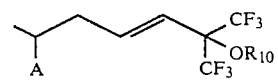

wherein A is as defined above and $R_{10}$ denotes a hydrogen atom, alkanesulfonyl group or arenesulfonyl group, is treated with a halogenating agent when $R_{10}$ is a hydrogen atom, or simply heated when $R_{10}$ is an alkanesulfonyl group or arenesulfonyl group, to give a compound represented by the general formula [35]

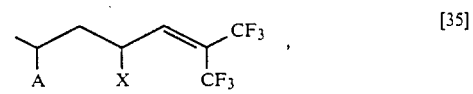

wherein A is as defined above and X denotes a halogen atom, alkanesulfonyloxy group or arenesulfonyloxy group.

Then, the compound [35] is reacted with hydrogen peroxide in the presence of a base to give the compound [14], which is then reduced and, if necessary, a protecting group is introduced to the resulting product to give a compound represented by the general formula [36]

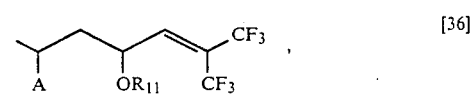

wherein A is as defined above and $R_{11}$ denotes a hydrogen atom or a protecting group.

Further, a compound represented by the general formula [37]

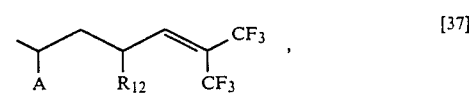

wherein A is as defined above and $R_{12}$ denotes a halogen atom, alkanesulfonyloxy group, arenesulfonyloxy group, hydroxyl group or protected hydroxy group, which includes the compounds [35] and [36], can be oxidized with a permanganate under acidic conditions to give the compound [39]

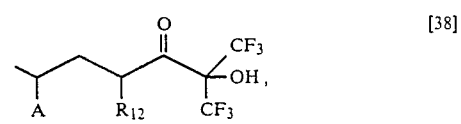

wherein A and $R_{12}$ are as defined above; or it can be oxidized with a permanganate in the presence of a base to give the compound [39]

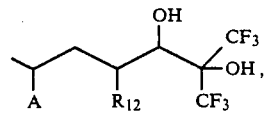

wherein A and $R_{12}$ are as defined above.

Further, the compound [26] included in the compound [39] is treated by the above-mentioned method to give the compound [29] and then optionally subjected to a deprotection reaction to prepare a compound represented by the general formula [40]

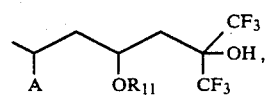

wherein A and $R_{11}$ are as defined above.

Although sometimes all or part of the protecting groups for the hydroxyl group will detach themselves depending on the kinds of the protecting groups and the reagents, reaction conditions etc. used in each step of the preparation process mentioned above, it is needless to say that in such cases the protecting group can be reintroduced by subjecting the product to reprotection reaction as occasion demands.

Thus, the compound [2] is obtained and further the compound [1] is prepared. Not only the objective compound [1] of this invention but also every intermediate compound formed in each of the above-mentioned reaction steps is a novel compound not described in the literature.

The compound [1'] thus obtained is administered parenterally, for example by intramuscular or intravenous injection, or orally, or as suppositories, or further by application to the skin as external remedies. The dosage can be appropriately selected depending on the method of administration within the range from 0.002 to about 100 μg, preferably 0.01 to 20 μg per one day for adult. In oral administration, for example, the dosage can be determined in the range from 0.01 to 50 μg, preferably 0.02 to 10 μg.

The pharmaceutical preparations of the compound [1] are prepared in combination thereof with pharmaceutically acceptable carries known to the art, which carries may be either solid or liquid. Specific examples of carriers to be used include maize starch, olive oil, sesame oil, and a triglyciride of medium chain fatty acid generally called MCT. The dosage forms used include, for example, tablets, capsules, liquids, powders, granules and creams.

Now, the pharmacological effect of the compound of this invention will be described below by way of experimental data.

The activity in bone calcium mobilization and increasing intestinal calcium transport of the compound of this invention in vitamin D-deficient rats Experimental method A 95% ethanol solution of the compound or 95% ethanol alone (for control groups) were administered intrajugularly to vitamin D-deficient rats. Blood was collected after 24 hours, and the concentration of calcium in serum was determined by the OCPC (orthocresolphthalein complexon) method. The intestinal calcium transport activity was determined by the method of Martin and Deluca (D. L. Martin and H. F. DeLuca, Am. J. Physiol., 216, 1351-1359 (1969)).

Results of experiments

The results of experiments are shown in Table 1.

TABLE 1

| | | Bone calcium mobilization response and intestinal calcium transport response in vitamin D-deficient rats | |
|---|---|---|---|
| | | (24 hours after administration) | |
| Compound | Dose (pmol/ 100 g body wt.) | Serum calcium (mg/100 ml) | Intestinal calcium transport (Ca [S/M]) |
| Control | — | 4.8 ± 0.29 | 2.6 ± 0.27 |
| 1α,25-(OH)₂D₃*⁾ | 50 | 5.5 ± 0.30* | 3.4 ± 0.72** |
| Compd. of this invention (6b) | 50 | 6.3 ± 0.55** | 8.9 ± 2.81** |
| Compd. of this invention (10) | 50 | 6.5 ± 0.40** | 6.5 ± 1.92** |
| Control | — | 4.8 ± 0.31 | 2.5 ± 0.30 |
| 1α,25-(OH)₂D₃*⁾ | 650 | 8.5 ± 0.59** | 3.6 ± 0.52 |
| Compd. of this invention (28a) | 650 | 7.2 ± 0.67** | 6.3 ± 1.88** |
| Compd. of this invention (28b) | 650 | 5.6 ± 0.60 | 5.7 ± 1.92** |

Mean ± SD (N = 4~6)
*, **P < 0.05, P > 0.01 against control
*⁾1α,25-Dihydroxyvitamin D₃

Differentiation of human premyeloblast leukemia cells (HL-60) into macrophages induced by the compound of this invention Experimental method Proliferation-suppression rate An HL-60 cell fluid adjusted to a concentration of 5×10⁴ cells/ml was incorporated with each of the agents to be tested and cultivated in a carbon dioxide incubator at 37° C. for 4 days. After the cultivation, the number of cells was measured by means of a Coulter counter. The percentage of the number thus measured relative to the number of cells in an untreated group was calculated, from which the proliferation-suppression rate was obtained.

NBT reduction

HL-60 cells were treated with the agent to be tested for 4 days, and then a growth medium (95% RPMI-1640, 5% FCS) and a 0.2% NBT solution containing 200 ng/ml of TPA (12-o-tetradecanoylphorbol-13-acetate) were added thereto in an equal amount, and the resulting mixture was incubated at 37° C. for 30 minutes. Thereafter, the cells were smeared onto a slide glass, subjected to Giemsa staining, and the coloration of the cells was examined under a microscope. The number of cells containing intracellular blue-black formazan deposits was measured for 200 cells, and the results were expressed in terms of the percentage of NBT reduction-positive cells.

Results of experiments

The results of the experiments are shown in Table 2

TABLE 2

| Compound | | Concn. (ng/ml) | Proliferation-suppression rate (%) | NBT reduction rate (%) |
|---|---|---|---|---|
| Control | | | 0 | 0.5 |
| 1α,25-(OH)$_2$D$_3$*) | | 10 | 72.4 | 56.5 |
| | | 1 | 36.1 | 16.5 |
| | | 0.1 | 6.2 | 1.0 |
| Compound of this invention | (6a) | 10 | 83.7 | 86.0 |
| | | 1 | 74.9 | 55.0 |
| | | 0.1 | 30.7 | 8.0 |
| | (6b) | 10 | 90.4 | 83.5 |
| | | 1 | 84.7 | 79.5 |
| | | 0.1 | 50.2 | 32.0 |
| | (10) | 10 | 89.9 | 82.5 |
| | | 1 | 78.6 | 46.0 |
| | | 0.1 | 45.9 | 12.5 |
| | (28a) | 10 | 92.2 | 80.0 |
| | | 1 | 76.4 | 60.5 |
| | | 0.1 | 19.8 | 6.5 |
| | (28b) | 10 | 86.9 | 81.0 |
| | | 1 | 67.3 | 60.0 |
| | | 0.1 | 22.8 | 2.0 |

*) 1α,25-Dihydroxyvitamin D$_3$

PREFERRED EMBODIMENTS OF THE INVENTION

This invention will be described in more detail below with reference to Examples. In the Examples, AC denotes the acetyl group, Ms denotes the methanesulfonyl group, and B and B' denotes a steroid residue represented by the general formula

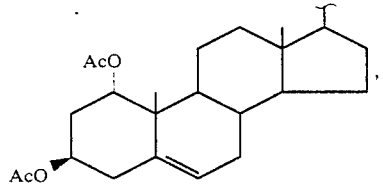

B

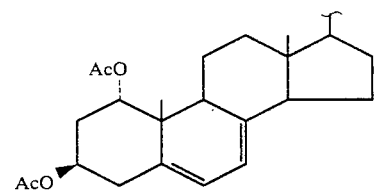

B' wherein Ac denotes the acetyl group.

EXAMPLE 1

Preparation of 24(S)-26,26,26,27,27,27-hexafluoro-1α,24,25-trihydroxyvitamin D$_3$(6a)

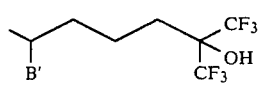

(1)

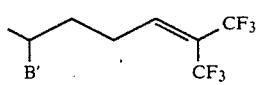

(2)

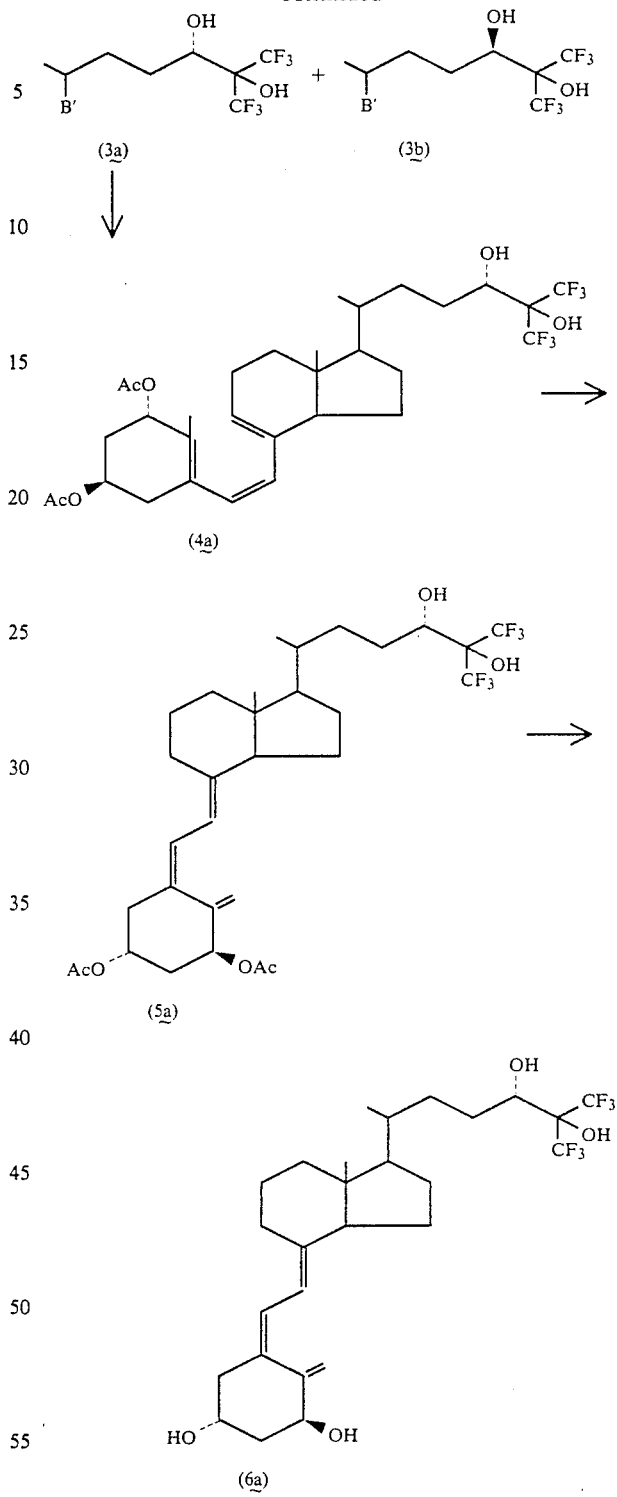

(1) Preparation of compound (2)

A solution of 600 mg of 1α,3β-diacetoxy-26,26,26,27,27,26-hexafluoro-25-hydroxycholesta-5,7-diene (1) synthesized by substantially the same method as described in Japanese National Publication (Kohyo) No. 501,176/83, 1 g of triphenylphosphine and 3 ml of carbon tetrachloride in 30 ml of 1,2-dichloroethane was heated under reflux in nitrogen atmosphere for 15 minutes. The reaction mixture was cooled down to room temperature, concentrated under reduced pressure, and the residue was subjected to silica gel column chromatography. Fractions eluted with ethyl acetate-n-hexane (1:10) was collected and recrystallized from methanol to obtain 560 mg (96% yield) of the intended 5,7,24-triene compound (2).

m.p. 116°–118° C.

IR (Nujol, cm$^{-1}$) 1735, 1670

NMR (CDCl3, δ): 0.62(3H, s), 0.98(3H, d, J=6.6 Hz), 1.01 (3H, s), 2.03(3H, s), 2.09(3H, s), 5.00(2H, m), 5.40(1H, m), 5.68(1H, m), 6.73(1H, t, J=8.0 Hz)

UV (EtOH, nm): λmax 271.5, 281, 293

(2) Preparation of compounds (3a) and (3b)

One hundred milliliters of acetone and 400 mg of potassium carbonate were added to 487 mg of the compound (2). While the mixture was being maintained at −15° C. in an ice-salt bath, 117 mg of potassium permanganate was added thereto, and the mixture was stirred for 1 hour. The mixture was further stirred at 0° C. for 30 minutes, then solvent was removed therefrom, and 100 ml of ethyl acetate and 100 ml of 1N hydrochloric acid were added to the residue and stirred. The mixture was filtered to remove manganese dioxide and the filtrate was separated into layers. The organic layer was washed once with 50 ml of a 3% aqueous sodium bicarbonate solution, then twice with 100 ml of water, and extracted with ethyl acetate. The reaction product was subjected to silica gel column chromatography and eluted with n-hexane-ethyl acetate mixture (10:1) to obtain 235 mg (46% yield) of a mixture of the compounds (3a) and (3b)

(CDCl3, δ)

0.62 (3H, s), 0.96 and 0.97(respectively 1.5H, d, J=6.0 Hz) 1.01(3H, s), 2.04(3H, s), 2.08(3H, s), 3.91(1H, t, J=12.3 Hz), 4.99(2H, m), 5.39(1H, d, J=3.0 Hz), 5.68(1H, d, J=3.0 Hz)

This product showed two peaks of the same area ratio at 5.1 minutes and 5.8 minutes in high-performance liquid chromatography (column: Zorbax BP SIL ® 4.6 mmφ×15 cm, carrier: ethyl acetate - n-hexane 1:6, flow rate: 2.5 ml/minute). A 100 mg portion of this product was subjected again to silica gel column chromatography and eluted with n-hexane-ethyl acetate (10:1). The eluted product was separated into an isomer (3a) of low polarity and an isomer (3b) of high polarity. Thus, 23 mg of the pure isomer (3a) and 5.1 mg of the pure isomer (3b) were obtained. Examination of the compound (3a) by X-ray crystallographic analysis confirmed that its 24-position was in S-configuration.

Isomer (3a)

NMR (CDCl3, δ): 0.62(3H, s), 0.97(3H, d, J=6.3 Hz), 1.01 (3H, s), 2.04(3H, s), 2.09(3H, s), 2.65(1H, m), 3.88(1H, d-d, J=9.2 Hz, 10.2 Hz), 4.24(1H, s), 4.99(1H, m), 5.00(1H, d, J=4.0 Hz), 5.39(1H, d-t, J=5.6 Hz, 3.0 Hz), 5.68(1H, d-d, J=3.3 Hz, 5.6 Hz)

Isomer (3b)

NMR (CDCl3, δ):
0.63(3H, s), 0.96(3H, d, J=6.3 Hz), 1.01(3H, s), 2.04(3H, s), 2.09(3H, s), 2 66(1H, m), 3.94(1H, d-d, J=8.3 Hz, 10.2Hz), 4.24(1H, s), 4.99(1H, m), 5.00(1H, d, J=3.6 Hz), 5.39(1H, d-t, J=5.6 Hz, 3.0 Hz), 5.68(1H, d-d, J=2.7 Hz, 5.6 Hz)

(3) Preparation of compound (6a)

Ten milligrams of the low polarity isomer (3a) of the compound (3) was dissolved in a mixture of 250 ml of benzene and 80 ml of ethanol, and irradiated with ultraviolet light by use of a 160 W low pressure mercury lamp under a nitrogen stream at 0° to 5° C. for 20 minutes. The resulting solution was refluxed for 4 hours, and the solvent was distilled off under reduced pressure to obtain the crude product of the compound (5a). The crude product was dissolved in 200 ml of methanol, 0.5 g of potassium hydroxide was added thereto, and the resulting mixture was stirred at room temperature for 1 hour to effect deacetylation. The reaction liquid was mixed with water and tracted with ethyl acetate. The extract was washed with water, dried over MgSO4 and concentrated. The residue was fractionally purified by means of high performance liquid chromatography (column: Zorbax BP SIL ® 2.0 cmφ×25 cm, carrier: ethyl acetate-n-hexane 2:1, flow rate: 8.0 ml/minute) to give 1.5 mg (17% yield) of the intended compound (6a). The product gave a retention time of 7.4 minutes in high performance liquid chromatography (column: Zorbax BP SIL ® 4.6 mmφ×15 cm, carrier: isopropanol-n-hexane 1:5, flow rate: 1.0 ml/minute).

NMR (CDCl3, δ)

0.55(3H, s), 0.96(3H, d, J=6.6 Hz), 1.25(3H, s), 2.33(1H, m), 2.58(1H, m), 2.80(1H, m), 3.88(1H, d, J=10.9 Hz), 4.22(2H, m), 4.43(1H, m), 5.00(1H, s), 5.33(1H, s), 6.02(1H, d, J=11.2 Hz), 6 38(1H, d, J=11.2 Hz)

UV (EtOH, nm): λmax 265

EXAMPLE 2

Preparation of 24(R)-26,26,26,27,27,27-hexafluoro-1α,24,25-trihydroxyvitamin D3(6b)

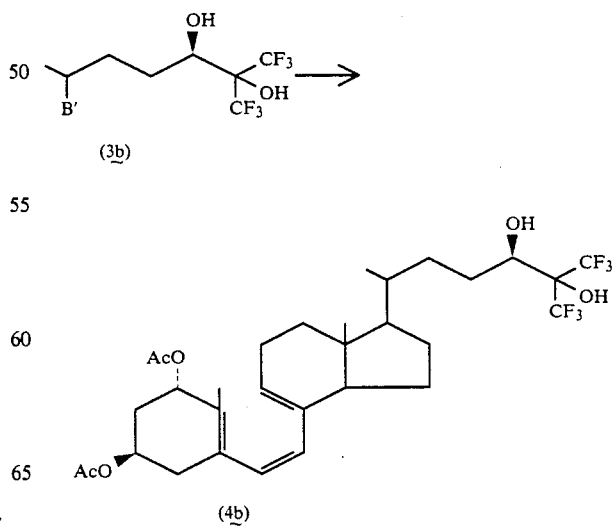

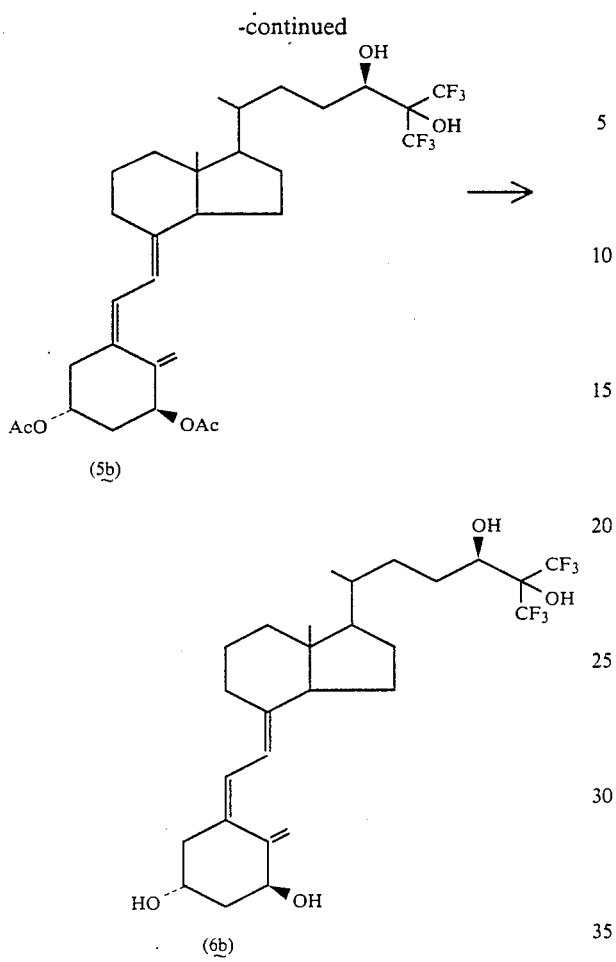

Three milligrams of the high polarity isomer (3b) of the compound (3) obtain in Example 1 was dissolved in a mixture of 340 ml of benzene and 90 ml of ethanol and irradiated with ultraviolet light by use of a 160 W low pressure mercury lamp under a nitrogen stream at 0° to 5° C. for 15 minutes. The resulting solution was refluxed for 4 hours and the solvent was distilled off under reduced pressure to obtain the crude product of the compound (5b). The crude product was dissolved in 100 ml of methanol, 0.2 g of potassium hydroxide was added thereto, and the resulting mixture was stirred at room temperature for 1 hour to effect deesterification. The reaction liquid was mixed with water and extracted with ethyl acetate. The extract was washed with water, dried over $MgSO_4$, and concentrated. The residue was fractionally purified by means of high performance liquid chromatography (column: Zorbax BP SIL ® 2.0 cm$\phi$×25 cm, carrier: ethyl acetate-n-hexane 2:1, flow rate: 8.0 ml/minute) to obtain 0.3 mg (12% yield) of the intended compound (6b). The product gave a retention time of 7.3 minutes in high performance liquid chromatography (column: Zorbax BP-SIL ® 4.6 mm$\phi$×15 cm, carrier: isopropanol-n-hexane 1:5, flow rate: 1.0 ml/minute).

NMR (CDCl$_3$, δ) 0.56(3H, s), 0.94(3H, d, J=5.6 Hz), 3.75(1H, d, J=11.9 Hz), 4.43(1H, m), 5.00(1H, s), 5.33(1H, s), 6.02(1H, d, J=10.5 Hz), 6.38(1H, d, J=10.5 Hz)

UV (EtOH, nm): λmax 265

EXAMPLE 3

Preparation of 1α,25-dihydroxy-26,26,26,27,27,27-hexafluoro-24-oxovitamin D$_3$ (10)

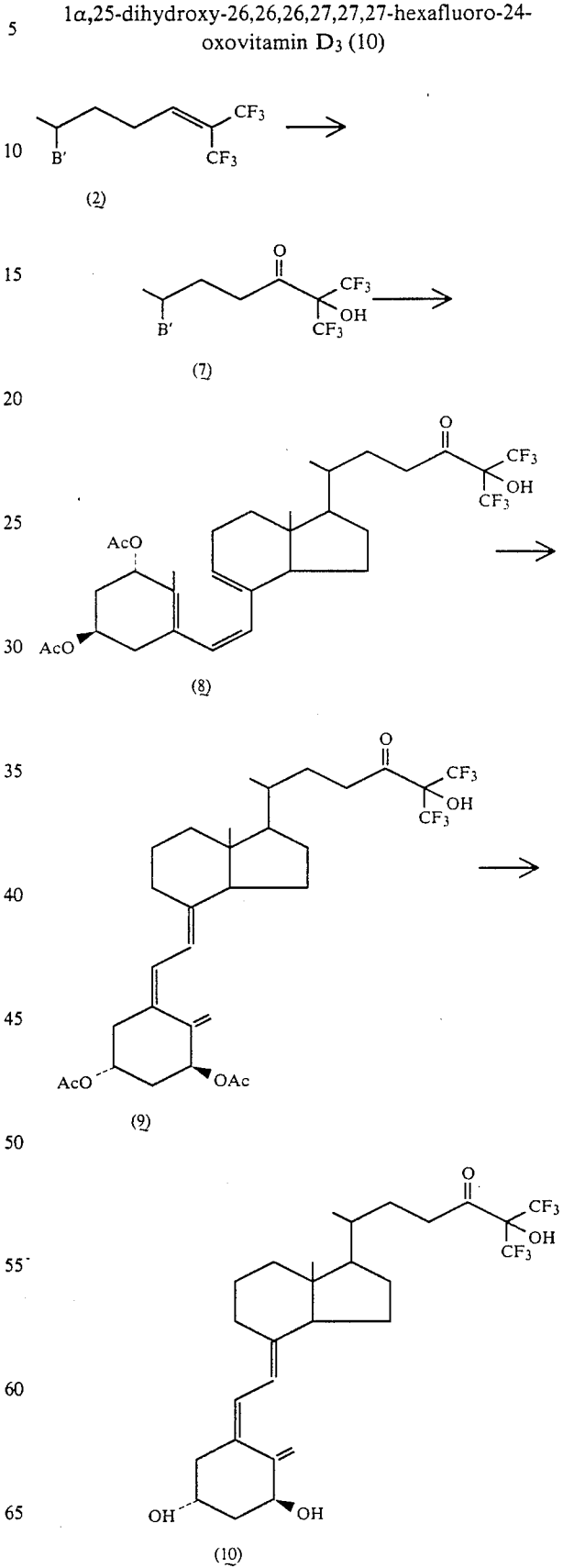

(1) Preparation of compound (7)

A 300 mg portion of 1α,3β-diacetoxy-26,26,26,27,27,27-hexafluorocholesta-5,7,24-triene (2) was dissolved in 150 ml of acetone, and 0.5 ml of glacial acetic acid was added thereto. While the mixture was being maintained at −15° C. in an ice-salt bath, 80 mg of potassium permanganate was added thereto, and the mixture was stirred for 2 hours. The mixture was further stirred at 0° C. for 30 minutes, 1 ml of methanol was added thereto, the resulting mixture was warmed up to room temperature, the solvent was removed under reduced pressure, and 100 ml of ethyl acetate and 100 ml of 1N hydrochloric acid were added to the residue and stirred. The mixture was filtered to remove manganese dioxide and the filtrate was separated into layers. The organic layer was washed once with 50 ml of 3% aqueous sodium bicarbonate solution, once with saturated aqueous sodium chloride solution, then twice with 100 ml of water. The organic layer was concentrated under reduced pressure. The residue was subjected to silica gel column chromatography, and eluted with n-hexane-ethyl acetate mixture (5:1) to obtain 233.4 mg (75% yield) of the compound (7)

NMR (CDCl$_3$, δ) 0.62(3H, s), 0.94(3H, d, J=5.6 Hz), 1.01(3H, s), 2.04(3H, s), 2.09(3H, s), 5.01(3H, m), 5.41(1H, m), 5.70(1H, m).

(2) Preparation of compound (10)

A solution of 34 mg of the compound (7) mentioned above in 150 ml of benzene and 350 ml of n-hexane was irradiated with ultraviolet light by using a 160 W low pressure mercury lamp under a nitrogen stream at 10° C. or below for 30 minutes. The resulting solution was refluxed for 3 hours and the solvent was distilled off under reduced pressure to obtain the crude product of the compound (9). The crude product was dissolved in 100 ml of methanol, 300 mg of sodium hydroxide was added thereto, and the mixture was stirred at room temperature for 2 hours to effect deacetylation. The reaction liquid was mixed with water and extracted with ethyl acetate. The organic layer was washed with water, dried over MgSO$_4$ and concentrated. The residue was subjected to high performance liquid chromatography (column: Zorbax BP-SIL 8 mmφ×25 cm, carrier: isopropanol-n-hexane 1:5, flow rate: 1.0 ml/minute) and the fraction of a retention time of 36 minutes was collected to obtain 4.2 mg (14% field) of the intended compound (10).

NMR (CDCl$_3$, δ)
0.55(3H, s), 0.94(3H, d, J=6.0 Hz), 1.25(3H, s), 2.31(1H, m), 2.60(1H, m), 4.24(1H, m), 4.43(1H, m), 5.00(1H, s), 5.33(1H, s), 6.02(1H, d, J=11.5 Hz), 6.37(1H, d, J=11.5 Hz)

UV (EtOH, nm): λmax 264, λmin 228

EXAMPLE 4

Preparation of 23(R)-26,26,26,27,27,27-hexafluoro-1α,23,25-trihydroxyvitamin D$_3$ (28a)

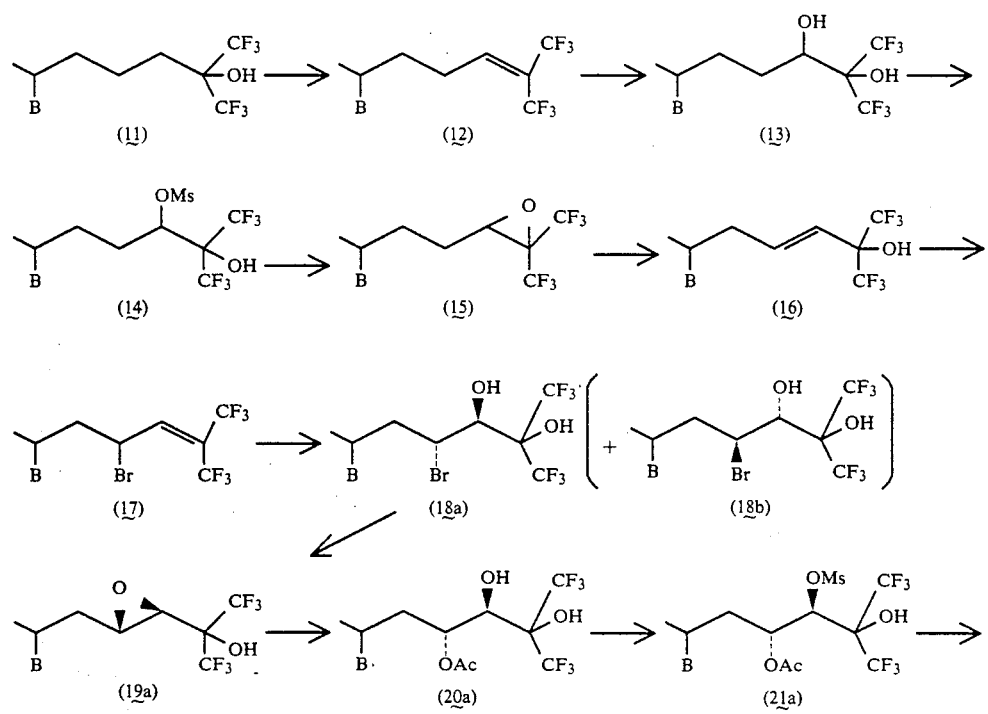

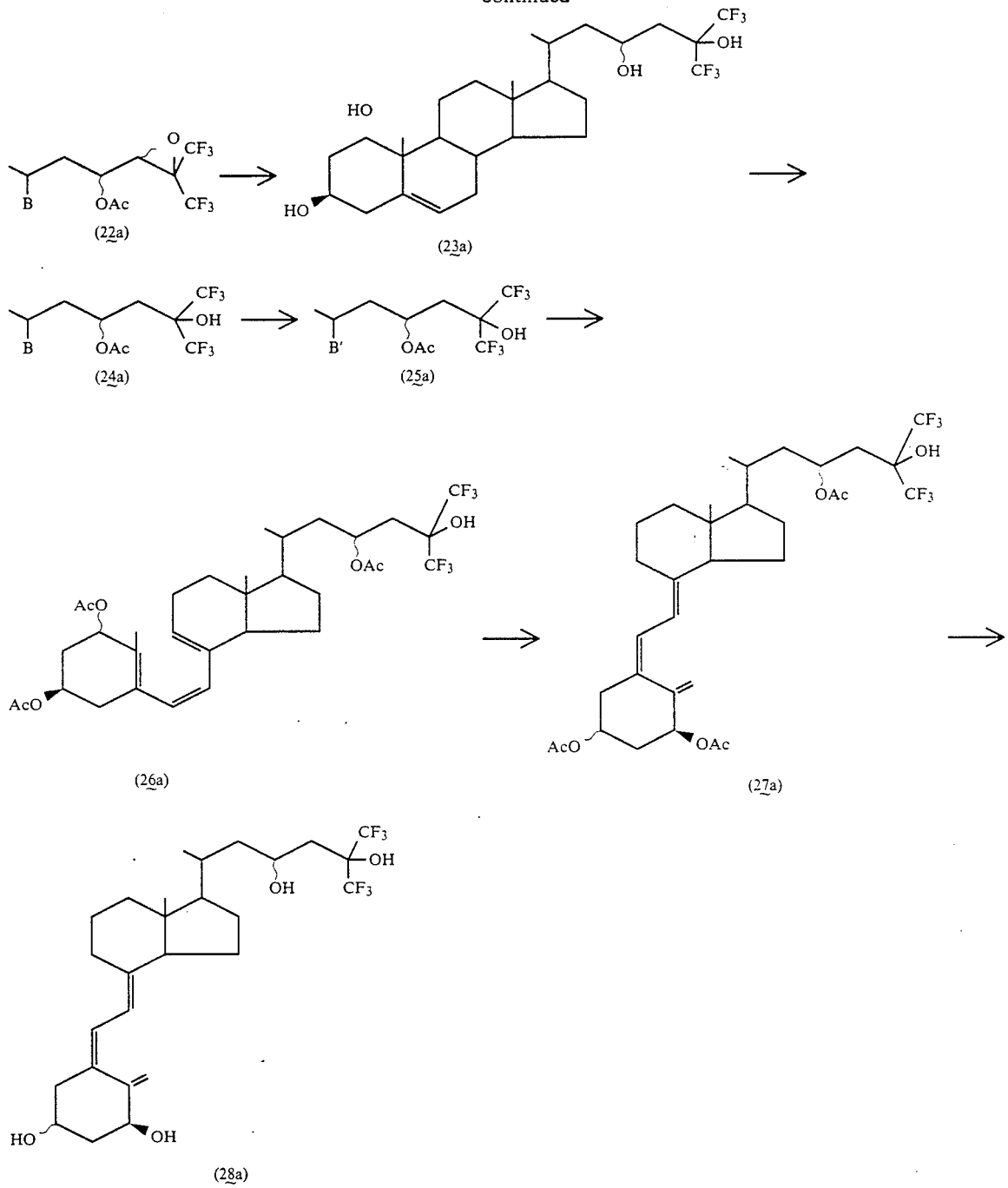

(1) Preparation of compound (12)

Forty grams of 1α,3β-diacetoxy-26,26,26,27,27,27-hexafluoro-25-hydroxycholest-5-ene (compound (11)) synthesized in substantially the same manner as in U.S. Pat. No. 4,358,406, 52 g of triphenylphosphine and 20 ml of carbon tetrachloride was dissolved in 1 l of 1,2-dichloroethane and the liquid mixture was stirred at 70° to 75° C. for 30 minutes. The reaction liquid was cooled down to room temperature and 200 g of powdery silica 9el was added thereto. The mixture was further stirred for 30 minutes and the silica gel was filtered off. The filtrate was concentrated under reduced pressure and the residue was purified by means of silica gel column chromatography (solvent system: ethyl acetate-n-hexane 1:10) and recrystallized from methanol to obtain 37 g (96% yield) of the compound (12).

M.p.: 96°–97° C.

IR (Nujol, cm$^{-1}$); 1740, 1735, 1670

NMR (CDCl$_3$, δ): 0.68(3H, s), 0.95(3H, d, J=6.6 Hz) 1.08(3H, s), 2.02(3H, s), 2.05(3H, s), 4.92(1H, m), 5.06(1H, b-s), 5.52(1H, m), 6.72(1H, t, J=7.7 Hz)

(2) Preparation of compound (13)

A liquid mixture of 10 g of the compound (12), 5 g of potassium carbonate and 1 l of acetone was cooled to −20° C., 2.67 g of potassium permanganate was added thereto under a nitrogen atmosphere, and the mixture was stirred at −20° to −15° C. for 5 hours. To the reaction liquid was added 300 ml of 2 N hydrochloric acid, the cooling both was removed, and the mixture was stirred until disappearance of the color of the reaction liquid. The reaction liquid was concentrated to about ⅓ the volume at 30° C. or below under reduced pressure and the residue was extracted with toluene. The toluene layer was washed with water, concentrated under reduced pressure and the residue was purified by silica gel column chromatography (eluent: ethyl acetate-n-hexane 1:4) to obtain 5.8 g (55% yield) of the compound (13) as a white powder.

NMR (CDCl$_3$, δ): 0.70(3H, b-s), 0.95(3H, m), 1.02(3H, s), 2.03(3H, s), 2.06(3H, s), 3.9(1H, m), 4.9(1H, m), 5.05(1H, b-s), (5.54(1H, m)

(3) Preparation of compound (15)

To a solution of 5 g of the compound (13) in 150 ml of pyridine, was added 3 ml of methanesulfonyl chloride and the mixture was allowed to stand at 5° C. for 20 hours. The reaction liquid was poured into 1 l of an ice-water mixture and extracted 3 times with 300 ml of ethyl acetate. The organic layer was washed successively with 1 N hydrochloric acid and water, and concentrated to obtain the compound (14).

The compound (14) was dissolved, without purification, in 100 ml of triethylamine and allowed to stand overnight at room temperature. The reaction liquid was mixed with 200 ml of toluene, and the mixture was concentrated under reduced pressure. The residue was purified by silica gel column chromatography (eluent: ethyl acetate-n-hexane 1:10) to obtain 4.38 g (91% yield) of the compound (15) as a white powder.

The IR spectrum of the product obtained showed no absorption due to the hydroxyl group.

(4) Preparation of compound (16)

To 200 ml of tetrahydrofuran solution containing 2.1 g of lithium diisopropylamide cooled to −10° C., was added 4.26 g of the above-mentioned epoxide (15) and the mixture was stirred at −10° to −5° C. for 50 minutes. The reaction liquid was extracted by adding thereto 50 ml of 1 N hydrochloric acid, 500 ml of saturated aqueous sodium chloride solution and 300 ml of ethyl acetate. The organic layer was washed with water and concentrated. The residue was purified by silica gel column chromatography (eluent : ethyl acetate-n-hexane 1:5) to obtain 3.81 g (89.5% yield) of the compound (16).

NMR (CDCl$_3$, δ):
0.68(3H, s), 0.89(3H, d, J=6.6 Hz), 1.08(3H, s), 2.03(3H, s), 2.06(3H, s), 3.30(1H, s), 4.9(1H, m), 5.05(1H, m), 5.53(1H, m), 5.57(1H, d, J=15.8), 6.27(1H, m)

(5) Preparation of compound (17)

In 200 ml of 1,2-dichloroethane were dissolved 3.65 g of the compound (16), 5.5 g of triphenylphosphine and 8 g of carbon tetrabromide, and the solution was stirred at 30° to 35° C. for 30 minutes. The reaction liquid was mixed with 80 g of powdery silica gel and stirred for 10 minutes. The silica gel was filtered off, and the filtrate was concentrated under reduced pressure. The residue was purified by silica gel column chromatography (eluent: ethyl acetate-n-hexane 1:12) to obtain 3.9 g (97% yield) of the compound (17). This compound was confirmed by means of NMR to be the equal-amount mixture of the R-isomer and the S-isomer of the 23-position.

NMR (CDCl$_3$, δ): 0.65*, 0.72** (respectively 1.5H, s), 0.95*, 0.96** (respectively 1.5H, d, J=6.5 Hz), 1.08*, 1.09** (respectively 1.5H, s), 2.03(3H, s), 2.06(3H, s), 4.8–5.0(1H, m), 5.05(1H, b-s), 5.53(1H, m), 6.65*, 6.81** (respectively 0.5H, d, J=11.5 Hz)

Among the above figures, those marked with * and ** refer to signals due to the 23(R)-isomer and the 23(S)isomer, respectively, and the others refer to signals common to both of the isomers.

(6) Preparation of compounds (18a) and (18b)

An equal-amount mixture, 1.34 g (2 mmol), of the two kinds of diastereomers of the brominated compound (17) obtained as described above was dissolved in 500 ml of acetone. The solution was cooled to −20° C., and 5 g of powdery potassium carbonate and 174 mg (1.1 mmol) of potassium permanganate were added thereto. The mixture was stirred at the same temperature until the violet color due to KMnO$_4$ disappeared. After completion of the reaction, the cooling bath was removed and 100 ml of 1N hydrochloric acid was added to the mixture. Acetone was distilled off from the mixture under reduced pressure and the residue was extracted with ethyl acetate. The organic layer was washed with water, concentrated under reduced pressure, and the residue was subjected to silica gel column chromatography. By elution with an ethyl acetate-n-hexane 1:10 mixture, 0.74 g of the unreacted starting material (17) was recovered. It was recrystallized from methanol to obtain 0.56 g of the compound (17) wherein the 23-position is in S-configuration. No 23(R) isomer was detected by NMR in the above product. Then, the fractions eluted with an ethyl acetate-n-hexane 1:4 mixture were collected and crystallized from an ethyl acetate-n-hexane mixture to obtain 0.54 g of the compound (18a)

NMR (CDCl$_3$, δ):
0.71(3H, s), 0.95(3H, d, J=6.6 Hz), 1.09(3H, s), 2.03(3H, s), 2.06(3H, s), 3.09(1H, d, 5.0 Hz), 4.05(1H, s), 4.28(1H, m), 4.64(1H, m), 4.9(1H, m), 5.06(1H, b-s), 5.54(1H, m),

Then, 536 mg of the recovered compound (17) wherein the 23-position has S-configuration was reacted with 139 mg of potassium permanganate in the same manner as described above in the presence of 3 g of powdery potassium carbonate and in 200 ml of acetone, and the reaction mixture was treated in the same manner as that for the compound (18a) to obtain 271 mg (48% yield) of the compound (18b).

NMR (CDCl$_3$-D$_2$O, δ): 0.69(3H, s), 0.97(3H, d, J=6.5 Hz), 1.08(3H, s), 2.03(3H, s), 2.06(3H, s), 4.3(1H, m), 4.69(1H, b-s), 4.9(1H, m), 5.06(1H, b-s), 5.53(1H m)

(7) Preparation of compound (19a) the compound (18a)

obtained as described above, 30 ml of toluene and 30 ml of 0.1N aqueous sodium hydroxide solution, was added 0.3 mg of a 10% aqueous tetra-n-butylammonium hydroxide solution. The reaction liquid was refluxed for 2 hours, cooled down to room temperature, and separated into layers. The toluene layer was washed successively with 1N hydrochloric acid and water and concentrated under reduced pressure. The residue was purified by silica gel column chromatography (eluent: ethyl acetate-n-hexane 1:6) to obtain 392 mg (92% yield) of the compound (19a).

NMR (CDCl$_3$, δ): 0.69(3H, s), 1.06(3H, d, J=6.6 Hz), 1.09(3H, s), 2.03(3H, s), 2.06(3H, s), 3.14(1H, m), 3.18(1H, b-s), 3.33(1H, b-s), 4.9(1H, m), 5.09(1H, b-s), 5.53(1H, m)

(8) Preparation of compound (20a)

To a solution of 365 mg of the compound (19a) in 10 ml of acetic acid were added 1 ml of acetic anhydride and 0.5 g of concentrated sulfuric acid and the mixture was allowed to stand at room temperature until disappearance of the starting compound (19a) as judged by PLC. The reaction liquid was poured into 200 ml of an ice-water mixture and extracted with toluene. The toluene layer was washed successively with water, a 5% aqueous sodium becarbonate solution and water and concentrated under reduced pressure. The residue was purified by silica gel column chromatography (eluent: ethyl acetate-n-hexane 1:5) to obtain 300 mg (75% yield) of the compound (20a).

NMR (CDCl$_3$-D$_2$O, δ): 0.67(3H, s), 0.91 (3H, d, J=6.5 Hz), 1.08(3H, s), 2.03(3H, s), 2.06(3H, s), 2.10(3H, s), 4.27(1H, b-s), 4.9(1H, m), 5.05(1H, b-s), 5.20(1H, m), 5.53(1H, m)

(9) Preparation of compound (22a)

In 10 ml of pyridine were dissolved 250 mg of the compound (20a) and 0.5 ml of methanesulfonyl chloride, and the solution was allowed to stand at 5° C. for 24 hours. The reaction liquid was mixed with water and extracted with toluene. The toluene layer was washed with 1N hydrochloric acid and water and concentrated to obtain a crude compound (21a)

The compound (21a) obtained above was dissolved in 10 ml of triethylamine and allowed to stand overnight at room temperature. To the reaction liquid was added 20 ml of toluene and the mixture was concentrated under reduced pressure. The residue was purified by silica gel column chromatography (eluent: ethyl acetate-n-hexane 1:5) to obtain 214 mg (88% yield) of the compound (22a).

NMR (CDCl$_3$, δ): 0.66(3H, s), 0.93(3H, d, J=6.3 Hz), 1.08(3H, s), 2.02(3H, s), 2.06(3H, s), 2.10(3H, s), 3.46(1H, d, J=7.3 Hz), 4.9(2H, m), 5.06(1H, b-s), 5.53(1H, m)

(10) Preparation of compound (23a)

To 20 ml of anhydrous tetrahydrofuran was added 150 mg of lithium aluminum hydride and the mixture was cooled to 5° C. Then, 200 mg of the above-mentioned compound (22a) was added to the suspension and stirred at 0° to 5° C. for 30 minutes. Then, 50 ml of water and 100 ml of 1N hydrochloric acid were added to the reaction mixture and the resulting mixture was extracted with ethyl acetate. The organic layer was washed with water and concentrated. The residue was washed with n-hexane and dried to obtain 154 mg (93% yield) of the compound (23a).

NMR (CDCl$_3$+D$_6$-acetone, δ): 0.70(3H, s), 0.98(3H, d, J=6.3 Hz), 1.03(3H, s), 3.84(1H, m), 3.95(1H, m), 4.31(1H, m), 5.57(1H, m)

(11) Preparation of compound (24a)

To 10 ml of pyridine were added 120 mg of the compound (23a) and 2 ml of acetic anhydride, and the mixture was allowed to stand at room temperature for 20 hours. Then, 100 ml of water was added to the reaction liquid and the mixture was extracted with toluene. The toluene layer was washed with 1N hydrochloric acid and concentrated under reduced pressure. The residue was dissolved in 10 ml of ahydrous tetrahydrofuran, 0.5 g of tetra-n-butylammonium fluoride was added to the solution, and the mixture was allowed to stand at room temperature for 15 minutes. It was then extracted by adding 50 ml of toluene and 100 ml of 1N hydrochloric acid. The toluene layer was washed with water and concentrated under reduced pressure. The residue was purified by silica gel column chromatography (eluent: ethyl acetate-n-hexane 1:10) to obtain 120 mg (81% yield) of the compound (24a).

NMR (CDCl$_3$, δ): 0.68(3H, s), 0.90(3H, d, J=6.6 Hz), 1.08(3H, s), 2.y3(3H, s), 2.06(3H, s), 2.13(3H, s), 4.9(2H, m), 5.06(1H, b-s), 5.53(1H, m), 6.47(1H, s)

(12) Preparation of compound (25a)

To a solution of 100 mg of the compound (24a) in 10 ml of carbon tetrachloride was added 40 mg of N-bromosuccinic imide and the mixture was refluxed under a nitrogen stream for 20 minutes. The reaction mixture was concentrated under reduced pressure, 5 ml of 2,4,6-collidine and 10 ml of xylene were added to the residue, and the mixture was refluxed for 30 minutes. The reaction liquid was cooled down to room temperature, washed, with 1 N hydrochloric acid and water, and concentrated under reduced pressure. The residue was purified twice by silica gel column chromatography (eluent:ethyl acetate-n-hexane 1:10) to obtained 27 mg (27% yield) of the compound (25a).

NMR (CDCl$_3$, δ): 0.62(3H, s), 0.93(3H, d, J=6.6 Hz), 1.01(3H, s), 2.04(3H, s), 2.07(3H, s), 2.14(3H, s), 5.0(3H, m), 5.40(1H, d, J=7.9 Hz), 5.68(1H, d, J=7.9 Hz)

(13) Preparation of compound (28a)

To 300 ml of a benzene-hexane 7:3 mixture was dissolved 20 mg of the compound (25a) and the solution was cooled to 0°–5° C. Nitrogen gas was introduced into the reaction liquid for 10 minutes, and the liquid was irradiated with ultravoilet light by means of a 100 W high pressure mercury lamp. The reaction liquid was concentrated under reduced pressure at 15° C. or below and the residue was purified by silica gel column chromatography (eluent: ethyl acetate-n-hexane 1:13) to obtain the compound (26a). The compound (26a) was heated in 20 ml of ethyl acetate under reflux for 3 hours and then concentrated under reduced pressure to obtain the crude compound (27a). To the concentrated residue was added 10 ml of a 5% KOH methanol solution, and the mixture was allowed to stand at 5° C. for 24 hours. The reaction liquid was extracted by addition of 100 ml of 1N hydrochloric acid and 100 ml of ethyl acetate, and the organic layer was washed with water and heated under reflux in nitrogen gas stream for 2 hours. Then the reaction liquid was concentrated under reduced pressure and the residue was purified by silica gel column chromatography (eluent: ethyl acetate-n-hexane 2:3) to obtain 2.9 mg (18% yield) of the objective compound (28a). The product gave a retention time of 17.6 minutes in high performance liquid chromatography (column : Zorbax BP SIL® 4.6 mmφ×25 cm, carrier: n-hexane-CH$_2$Cl$_2$-MeOH 50:50:3, flow rate: 2 ml/minute).

UV (EtOH, nm): λmax 264.5

NMR (CDCl$_3$, δ): 0.58(3H, s), 1.00(3H, d, J=6.3 Hz), 4.2–4.4(3H, m), 5.00(1H, s), 5.33(1H, s), 6.01(1H, d, J=10.5 Hz), 6.37(1H, d, J=10.5 Hz)

Example 5

Preparation of 23(S)-26,26,26,27,27,27-hexafluoro-1α,23,25-trihydroxyvitamin D₃ (28b)

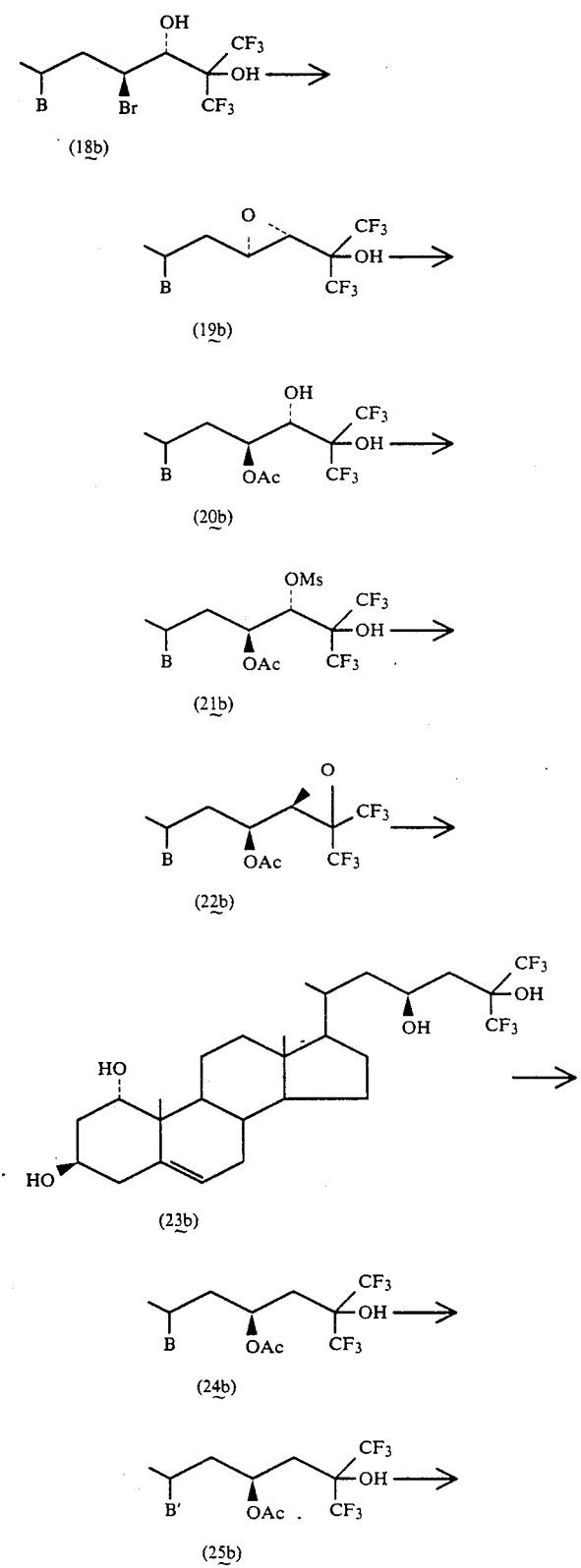

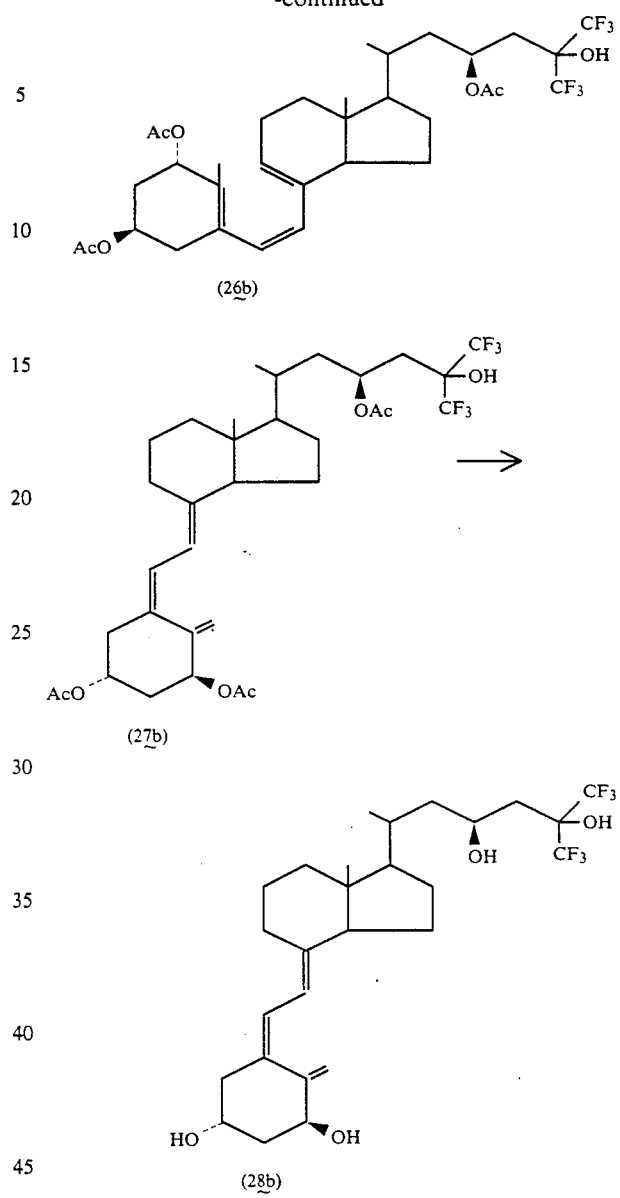

The compound (28b) was prepared in substantially the same manner as in Example 4 by using as the starting material the compound (18b) obtained in Example 4.

(1) Preparation of compound (19b)

From 260 mg of the compound (18b) obtained in Example 4, was obtained 200 mg (89% yield) of the compound (19b).

NMR (CDCl₃δ) 0.67(3H, s), 1.02(3H, s), 1.06(3H, d, J=6.6 Hz), 2.03(3H, s), 2.06(3H, s), 3.16(1H, m), 3.26(1H, b-s), 3.35(1H, s), 4.9(1H, m), 5.06(1H, b-s), 5.53(1H, m)

(2) Preparation of compound (20b)

From 195 mg of the compound (19b) was obtained 150 mg (70% yield) of the compound (20b).

NMR (CDCl₃-D₂O, δ) 0.67(3H, s), 0.94(3H, d, J=6.6 Hz), 1.08(3H, s), 2.03(3H, s), 2.06(3H, s), 2.11(3H, s), 4.2(2H, m), 4.9(1H, m), 5.05(1H, b-s), 5.11(1H, m), 5.53(1H, m)

(3) Preparation of the compound (22b)

From 80 mg of the compound (20b) was obtained 73 mg (94% yield) of the compound (22b).

NMR (CDCl$_3$, δ)
0.65(3H, s), 0.98(3H, d, J=6.0 Hz). 1.08(3H, s), 2.02(3H, s), 2.06(3H, s), 2.11(3H, s), 3.50(1H, d, J=8.9 Hz), 4.9(1H, m), 5.06(1H, b-s), 5.53(1H, m)

(4) Preparation of compound (23b)

From 70 mg of the compound (22b) was obtained 53 mg (90% yield) of the compound (23b).

NMR (CDCl$_3$+D$_6$-acetone, δ) 0.70(3H, s), 0.97(3H, d, J=6.2 Hz), 1.03(3H, s), 3.8(1H, m), 3.95(1H, m), 4.33(1H, m), 5.56(1H, m)

(5) Preparation of compound (24b)

From 50 mg of the compound (23b) was obtained 59 mg (96% yield) of the compound (24b).

NMR (CDCl$_3$, δ) 0.67(3H, s), 0.99(3H, d, J=6.6 Hz), 1.08(3H, s), 2.03(3H, s), 2.06(3H, s), 2.11(3H, s), 4.9(1H, m), 5.05(2H, b-s), 5.53(1H, m), 5.66(1H, s)

(6) Preparation of compound (25b)

From 55 mg of the compound (24b) was obtained 14 mg (25% yield) of the compound (25b).

NMR (CDCl$_3$, δ) 0.62(3H, s), 1.05(6H, m), 2.04(3H, s), 2.06(3H, s), 2.11(3H, s), in the vicinity of 5.0(3H, m), 5.40(1H, d, J=8.0 Hz), 5.67(1H, d, J=7.9 Hz)

(7) Preparation of compound (28b)

From 10 mg of the compound (25b) was obtained 1.1 mg (14% yield) of the objective compound (28b). The compound obtained showed a retention time of 15.4 minutes in high performance liquid chromatography (the conditions were the same as those for the compound (28a) of Example 4).

UV (EtOH, nm): λmax 265

NMR (CDCl$_3$, δ) 0.58(3H, s), 0.98(3H, d, J=6.5 Hz), 4.2-4.5(3H, m), 5.00(1H, s), 5.33(1H, s), 6.02(1H, d, J=10.6 Hz), 6.37(1H, d, J=10.4 Hz)

EXAMPLE 6

Preparation of 23(S), 24(S)-26,26,26,27,27,27-hexafluoro-1α,23,24,25-tetrahydroxyvitamin D$_3$ (39b)

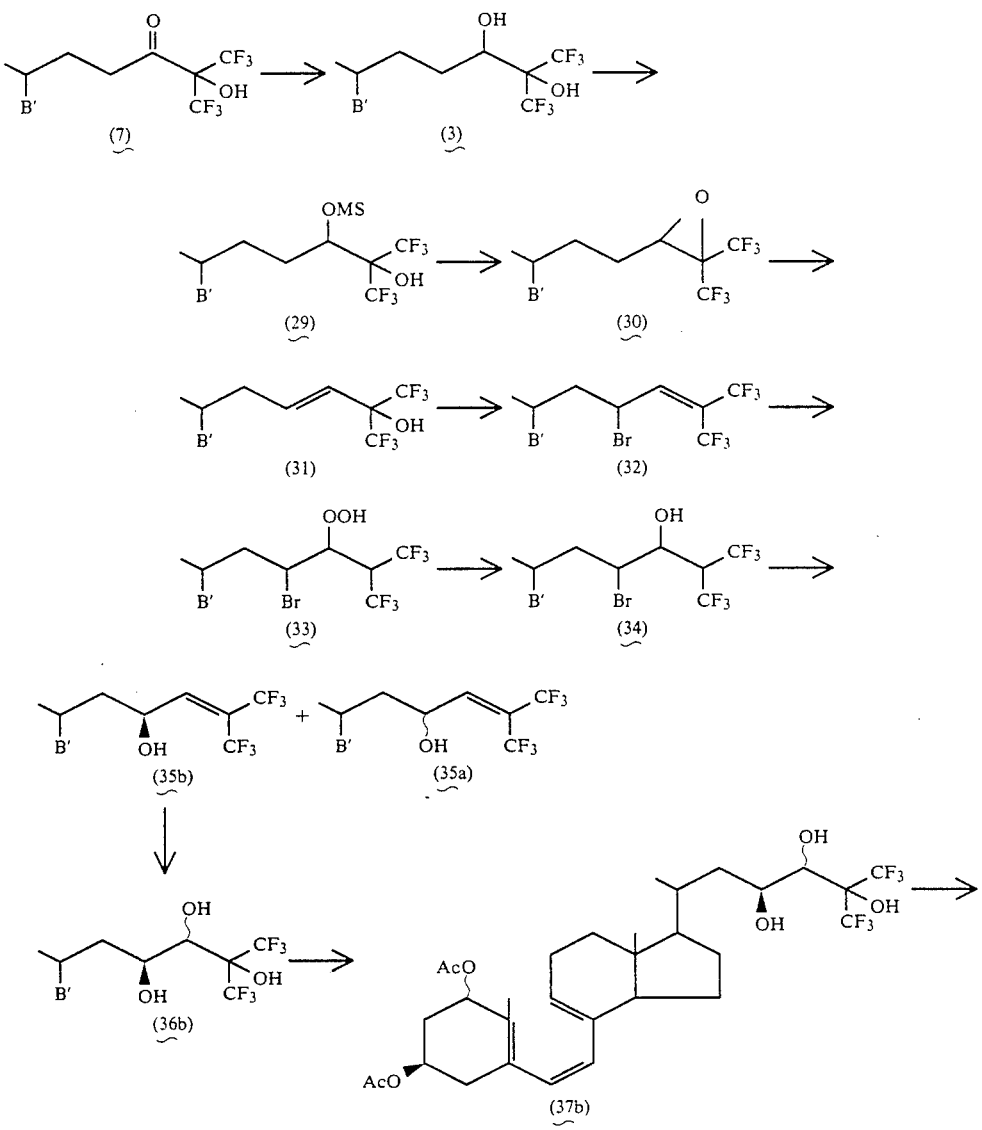

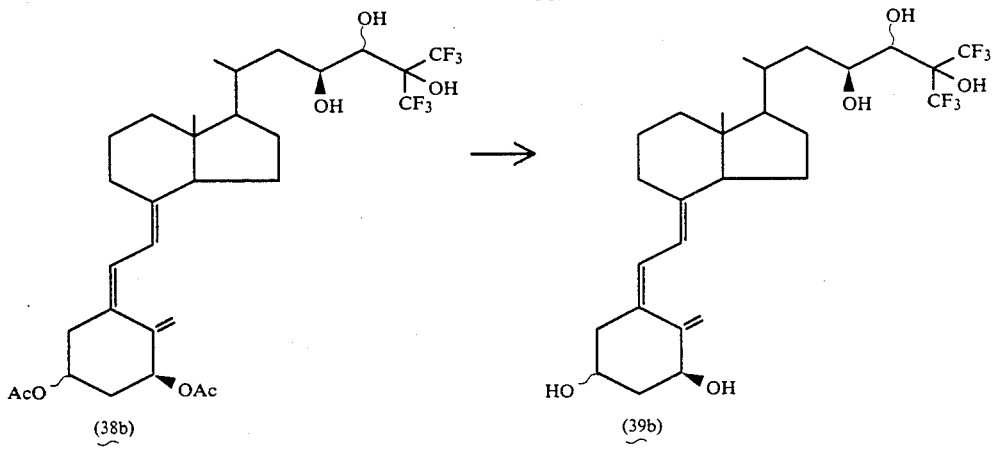

(38b) → (39b)

(1) Preparation of compound (3)

A 2.0 g portion of the compound (7) obtained in the same manner as in Example 3 was dissolved in 30 ml of trahydrofuran and the resulting solution was cooled to 0°-2° C. To the reaction liquid was added 0.5 g of NaBH$_4$. The resulting mixture was stirred at the same temperature for 30 minutes and then extracted by addition of water and benzene. The benzene layer was washed with water and then concentrated under reduced pressure to obtain 2.0 g (99% yield) of the compound (3). This product was confirmed by NMR and high performance liquid chromatography to correspond to the mixture of compounds (3a) and (3b) obtained in Example 1.

(2) Preparation of compound (30)

A 1.9 portion of the compound (3) was treated in the same manner as in the synthesis of the compound (15) of Example 4 to obtain the compound (29) and then 1.72 g (93% yield) of the compound (30).

NMR (CDCl$_3$, δ) 0.62(3H, s), 0.97(3H, d, J=6.6 Hz), 1.01(3H, s), 2.04(3H, s), 2.09(3H, s), 3.4(1H, m), 5.0(2H, m), 5.4(1H, m), 5.7(1H, m)

(3) Preparation of compound (31)

A 1.5 g portion of the epoxy compound (30) was treated in the same manner as in the synthesis of the compound (16) of Example 4 to obtain 1.2 g (80% yield) of the compound (31).

NMR (CDCl$_3$δ) 0.63(3H, s), 0.93(3H, d, J=6.6 Hz), 1.01(3H, s), 2.04(3H, s), 2.09(3H, s), 2.95(1H, s), 5.0(2H, m), 5.4(1H, m), 5.58(1H, d, J=15.5 Hz), 5.68(1H, m), (6.27(1H, m)

(4) Preparation of compound (32)

A 1.0 g portion of the compound (31) was treated in the same manner as in the synthesis of the compound (17) of Example 4 to obtain 1.0 g (91% yield) of the compound (32).

This product was confirmed by NMR to be a mixture of two kinds of diastereomers.

NMR (CDCl$_3$δ) 0.59, 0.67(respectively 1.5H, s), 0.96, 0.98(respectively 1.5H, d, J=6.6 Hz), 1.00, 1.02(respectively 1.5H, s), 2.04(3H, s), 2.09(3H, s), 5.0(3H, m), 5.39(1H, m), 5.68(1H, m), 6.65(0.5H, d, J=12 Hz), 6.82(0.5H, d, J=12 Hz)

(5) Preparation of compounds (35a) and (35b)

To a solution consisting of 670 mg of the brominated compound (32), 30 ml of methanol, 70 ml of tetrahydrofuran and 5 ml of 35% aqueous hydrogen peroxide solution was added 0.1 ml of 2 N NaOH solution and the resulting reaction liquid was allowed to stand at room temperature for 40 hours. The reaction liquid was mixed with aqueous sodium chloride solution and extracted with toluene. The toluene layer was washed with water and then concentrated to obtain a crude product of the compound (33). The crude product was dissolved in 50 ml of ethyl acetate, then 5 ml of water and 1 g of potassium iodide were added thereto, and the resulting mixture was stirred at 0° to 5° C. for 1 hour. The reaction liquid was washed successively with an aqueous Na$_2$S$_2$O$_3$ solution and water, and then concentrated under reduced pressure. The residue was purified by silica gel column chromatography to obtain 280 mg of the intended compound (34) while recovering 380 mg of the compound (32), the unreacted starting material.

The compound (34) obtained above was dissolved in 30 ml of toluene, then 10 ml of 0.1N aqueous NaOH solution and 0.2 ml of 10% aqueous tetrabutylammonium hydroxide solution were added thereto, and the resulting two-layer solution was stirred at room temperature for 30 minutes and then at 60° C. for 30 minutes. The reaction liquid was cooled down to room temperature and separated into layers. The toluene layer was washed with dilute hydrochloric acid and concentrated under reduced pressure. The residue was purified by silica gel column chromatography (eluent: ethyl acetate-n-hexane 1: 5) to obtain 40 mg of the compound (35a) of low polarity and 170 mg of the compound (35b) of high polarity.

NMR (CDCl$_3$, δ)

Compound (35a) 0.65(3H, s), 0.97(3H, d, J=6.6 Hz), 1.01(3H, s), 2.04(3H, s), 2.09(3H, s), 4.83(1H, m), 5.0(2H, m), 5.39(1H, m), 5.68(1H, m), 6.71(1H, d, J=8.6 Hz)

Compound (35b) 0.61(3H, s), 1.01(3H, s), 1.04(3H, d, J=6.0 Hz), 2.04(3H, s), 2.09(3H, s), 4.83(1H, m), 5.0(2H, m), 5.39(1H, m), 5.68(1H, m), 6.60(1H, d, J=9.2 Hz)

(6) Preparation of compound (36b)

A suspension consisting of 30.3 mg of the compound (35b), 0.5 g of potassium carbonate and 50 ml of acetone was cooled to −20 C, and 8 mg of KMnO$_4$ was added thereto. The reaction liquid was stirred at the same temperature for 3 hours, and extracted by addition of 30 ml of 2NHCl, 200 ml of aqueous sodium chloride solution and 150 ml of ethyl acetate. The organic layer was washed with water and then concentrated under reduced pressure. The residue was purified by silica gel column chromatography (eluent: ethyl acetate-n-hexane 1:3) to obtain 26.2 mg (41% yield) of the compound (36b).

NMR (CDCl$_3$, δ) 0.63(3H, s), 0.99(3H, d, J=6.6 Hz), 1.01(3H, s), 3.0(1H, d, J=9 Hz), 3.97(1H, d, J=9 Hz), 4.34(1H, m), 5.0(2H, m), 5.2(1H, s), 5.40(1H, m), (column:Zorbax BP SIL® 4.6 mmφ×25 cm, carrier:CH$_2$Cl$_2$-MeOH 25:1, flow rate: 1 ml/min).

UV (EtOH, nm): λmax 265, λmin 228

NMR (CDCl$_3$, δ) 0.56(3H, s), 1.00(3H, d, J=6.5 Hz), 3.96(1H, s), 4.23(1H, m), 4.34(1H, m), 4.42(1H, m), 5.00(1H, s), 5.33(1H, s), 6.02(1H, d, J=10.5HZ), 6.38(1H, d, J=10.5 Hz)

EXAMPLE 7

Preparation of 23(S)-26,26,26,27,27,27-hexafluoro-24-oxo-1α,23,25-trihydroxyvitamin D$_3$ (43b)

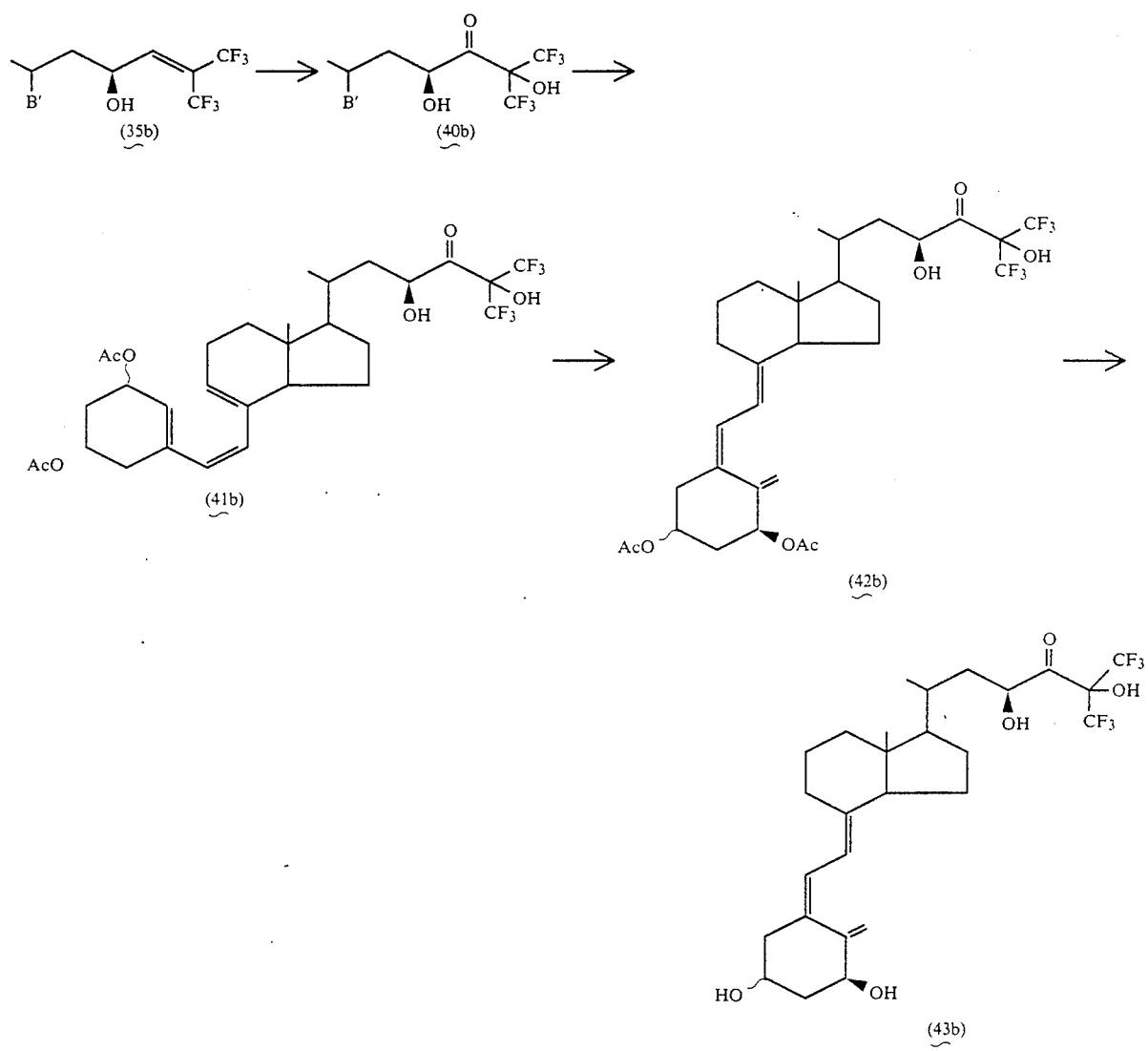

5.68(1H, m)

(7) Preparation of compound (39b)

In the same manner as in the synthesis of the compound (28a) of Example 4, 20 mg of the compound (36b) was irradiated with ultraviolet light to obtain the compound (37b), which was then subjected to thermal isomerization to obtain the compound (38b), which latter was hydrolyzed and finally purified by silica gel column chromatography (eluent:ethyl acetate-n-hexane 2:1) to obtain 2.6 mg (15% yield) of the objective compound (39b). The product showed a retention time of 13.3 minutes in high performance liquid chromatography

(1) Preparation of compound (40b)

A solution consisting of 60 mg of the compound (35b) obtained in Example 6, 1 ml of acetic acid and 30 ml of acetone was cooled to −15° C., 8 mg of KMnO$_4$ was added thereto, and the mixture was stirred at the same temperature for 2 hours. The reaction liquid was treated in the same manner as that for the compound (36b) of Example 6 to obtain 40.5 mg (71% yield) of the compound (40).

NMR (CDCl$_3$, δ) 0.62(3H, s), 1.01(3H, s), 1.07(3H, d, J=6.6 Hz), 2.04(3H, s), 2.09(3H, s), 2.92(1H, d, J=8.3

Hz), 4.72(1H, m), 5.0(2H, m), 5.41(1H, m), 5.60(1H, s), 5.68(1H, m)

(2) Preparation of compound (43b)

In the same manner as that for the compound (28a) of Example 4, 13 mg of the compound (40b) was irradiated with ultraviolet light, and then heated to give the compound (42b). The compound (42b) was dissolved in 20 ml of methanol, then 0.5 ml of concentrated hydrochloric acid was added thereto, and the resulting mixture was allowed to stand overnight in the dark at room temperature. The reaction liquid was extracted by addition of water and ethyl acetate. The organic layer was washed with water and then concentrated. The residue was purified by silica gel column chromatography to obtain 1.1 mg (10% yield) of the intended product (43b).

UV (EtOH, nm): max 265, min 227

NMR (CDCl$_3$, δ) 0.55(3H, s), 1.02(3H, d, J=6.5 Hz), 4.22(1H, m), 4.33(1H, m), 4.73(1H, m), 5.00(1H, s), 5.33(1H, s), 6.02(1H, d, J=10.9 Hz), 6.37(1H, d, J=10.4 Hz)

This product showed a retention time of 12.0 minutes in high performance liquid chromatography (the conditions therefor being the same as those for the compound (39b) of Example 6).

EXAMPLE 8

Preparation of 26,26,26,27,27,27-hexafluoro-23-oxo-1α,24,25-trihydroxyvitamin D$_3$ (47)

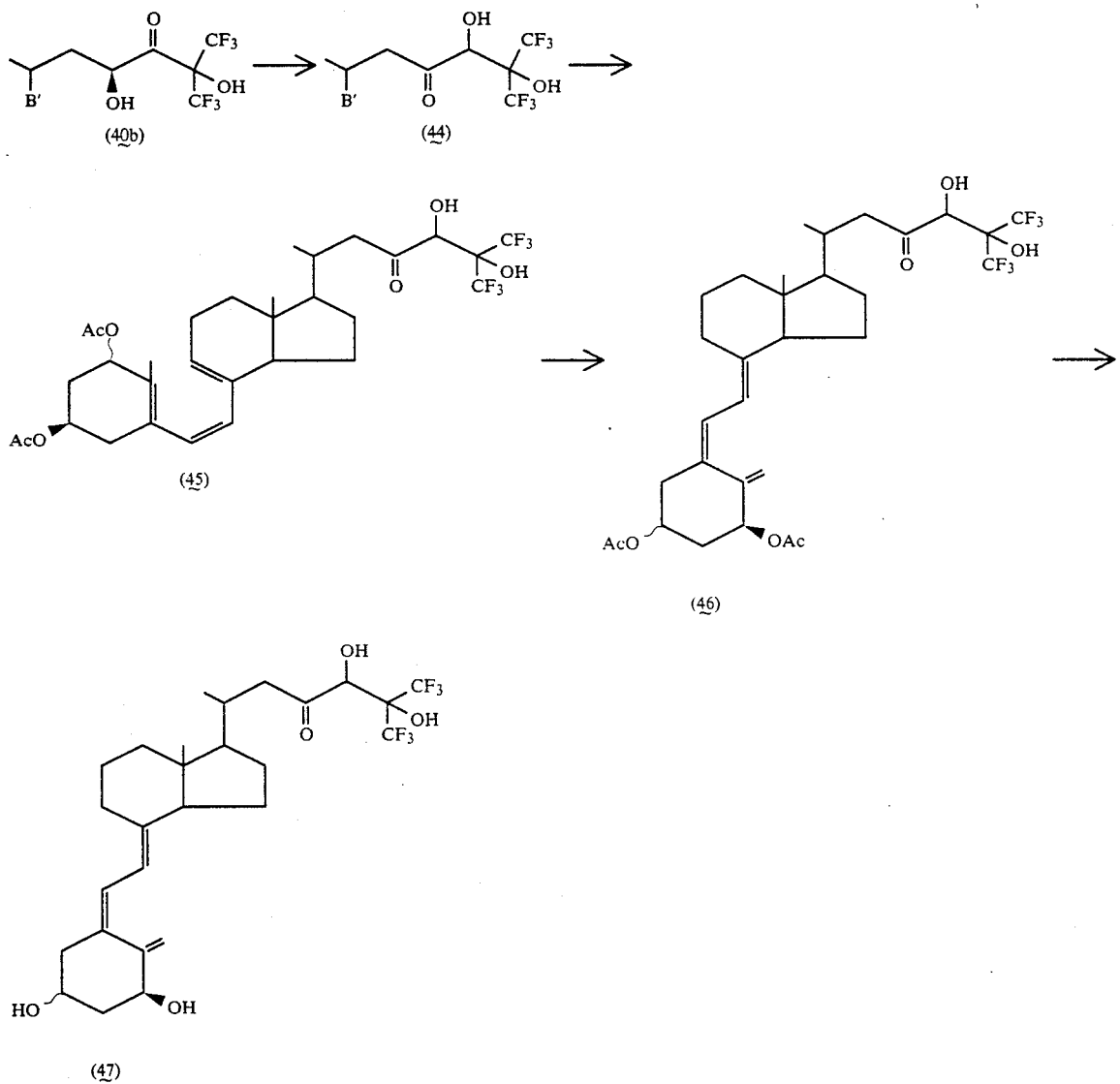

(1) Preparation of compound (44)

A solution consisting of 20 mg of the compound (40b) obtained in Example 7, 1 ml of s-collidine, and 3 ml of toluene was refluxed until the starting material (40b) had disappeared as examined by liquid chromatography. The reaction liquid was cooled down to room temperature, washed with dilute hydrochloric acid, and then concentrated under reduced pressure to obtain 20 mg of the compound (44). This product was confirmed by NMR and liquid chromatography to be a mixture of two kinds of diastereomers of 24R and 24S.

NMR (CDCl$_3$, δ) 0.66(3H, s), 0.87, 0.96(respectively 1.5H, d, J=6.7 Hz), 1.06(3H, s), 2.04(3H, s), 2.09(3H, s), 2.55-2.95(2H, m), 4.41, 4.46(respectively 0.5H, s), 5.0(2H, m), 5.41(1H, m), 5.68(1H, m)

mass spectrum: m/e 638 (M$^+$)

(2) Preparation of compound (47)

In the same manner as in the synthesis of the compound (43b) of Example 7, 10 mg of the compound (44) was subjected to ultraviolet irradiation, thermal isomerization and deacetylation, and finally purified by silica gel column chromatography (eluent: ethyl acetate-n-hexane 2:1) to obtain 0.6 mg (7% yield) of the intended product (47), a mixture of two kinds of diasteromers resulting from the asymmetric carbon atom of the 24-position.

UV (EtOH, nm): λmax 264.5

NMR (CDCl$_3$, δ) 0.56(3H, s), 4.33(1H, m), 4.2–4.5(2H, m), 5.01(1H, m), 5.34(1H, m), 6.01(1H, d, J=10.5 Hz), 6.38(1H, d, J=10.3 Hz)

This product showed a retention time of 10.9 minutes and 11.2 minutes in high performance liquid chromatography (the conditions therefor being the same as those for the compound (39b) of Example 6).

What is claimed is:

1. A compound represented by the formula

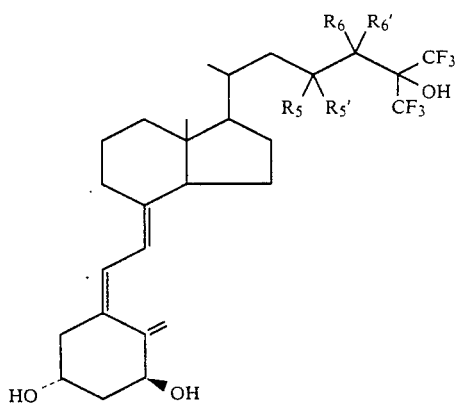

wherein R$_5$ and R$_6$ each denotes a hydrogen atom or a hydroxy group and R$_5'$ and R$_6'$ each denotes a hydrogen atom, or alternatively R$_5$ and R$_5'$ together or R$_6$ and R$_6'$ together denote an oxo group, provided that R$_5$, R$_5'$, R$_6$ and R$_6'$ cannot denote hydrogen atoms simultaneously and that when R$_5$ is a hydroxy group and R$_5'$ is a hydrogen atom, R$_6$ and R$_6'$ together cannot denote an oxo group.

2. 26,26,26,27,27,27-hexafluoro-1α,24,25-trihydroxyvitamin D$_3$.

3. 1α,25-dihydroxy-26,26,26,27,27,27-hexafluoro-24-oxovitamin D$_3$.

4. 26,26,26,27,27,27-hexafluoro-1α,23,25-trihydroxyvitamin D$_3$.

5. 26,26,26,27,27,27-hexafluoro-1α,23,24,25-tetrahydroxyvitamin D$_3$.

6. 26,26,26,27,27,27-hexafluoro-23-oxo-1α,24,25-trihydroxyvitamin D$_3$.

7. A compound represented by the formula

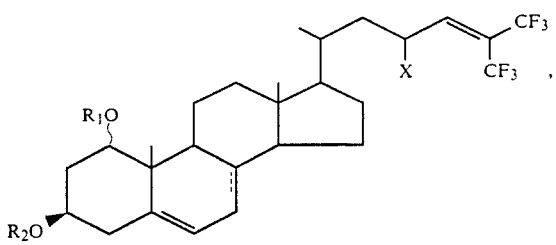

wherein R$_1$ and R$_2$ each denotes a hydrogen atom or a protecting group for the hydroxyl group; X denotes a halogen atom, alkanesulfonyloxy group or arenesulfonyloxy group; and the dotted line . . . between the carbon atoms of the 7- and the 8-position signifies the optional presence of a bond.

8. A process for producing a compound represented by the formula

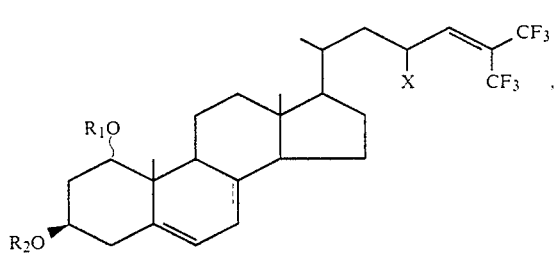

wherein R$_1$ and R$_2$ each denotes a hydrogen atom or a protecting group; X denotes a halogen atom, alkanesulfoynloxy group or arenesulfonyloxy group; and the dotted line . . . between the carbon atoms of the 7- and the -position signifies the optional presence of a bond, which comprises subjecting a compound represented by the formula

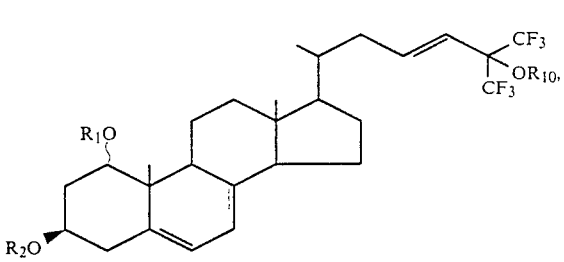

wherein R$_1$, R$_2$ and the dotted line . . . are as defined above; and R$_{10}$ denotes a hydrogen atom, alkanesulfonyl group or arenesulfonyl group, to a treatment with a halogenating agent when R$_{10}$ is a hydrogen atom, or to heating when R$_{10}$ is an alkanesulfonyl group or arenesulfonyl group.

9. A compound represented by the formula

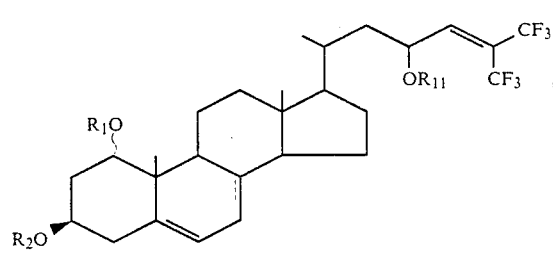

wherein $R_1$, $R_2$ and $R_{11}$ each denotes a hydrogen atom or a protecting group of the hydroxyl group; and the dotted line . . . between the carbon atoms of the 7- and the 8-position signifies the optional presence of a bond.

10. A process for producing a compound represented by the formula

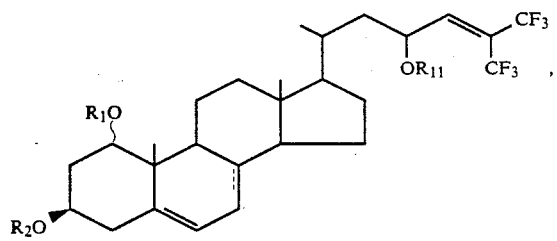

wherein $R_1$, $R_2$ and $R_{11}$ each denotes a hydrogen atom or a protecting group; and the dotted line . . . between the carbon atoms of the 7- and the 8-position signifies the optional presence of a bond, which comprises reacting a compound represented by the formula

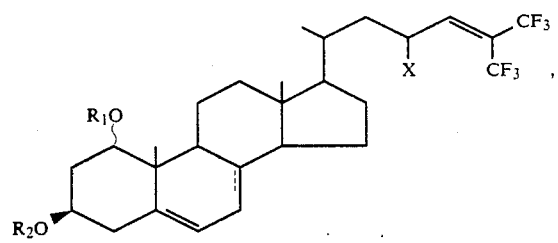

wherein $R_1$, $R_2$ and the dotted line . . . between the carbon atoms of the 7- and the 8-position are as defined above; and X denotes a halogen atom, alkanesulfonyloxy group or arenesulfonyloxy group, with hydrogen peroxide to give a compound represented by the formula

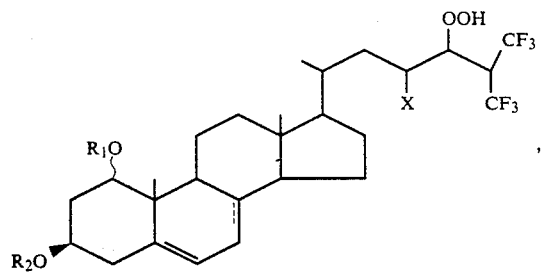

wherein $R_1$, $R_2$, X and the dotted line . . . are as defined above; then reducing it into a halohydrin compound represented by the formula

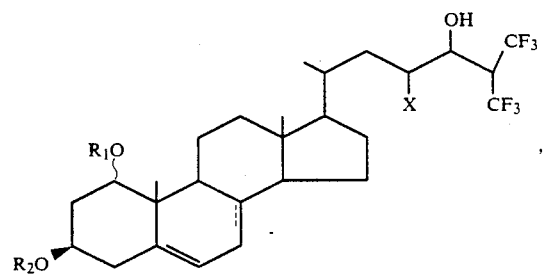

wherein $R_1$, $R_2$, X and the dotted line . . . are as defined above; treating the halohydrin compound with a base; and optionally subjecting the resulting product to a protecting reaction.

11. A compound represented by the formula

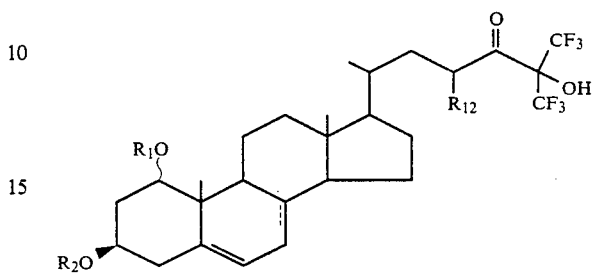

wherein $R_1$ and $R_2$ each denotes a hydrogen atom or a protecting group; $R_{12}$ denotes a halogen atom, alkanesulfonyloxy group, arenesulfonyloxy group, hydroxyl group or protected hydroxyl group; and the dotted line . . . between the carbon atoms of the 7- and the 8-position signifies the optional presence of a bond.

12. A process for producing a compound represented by the formula

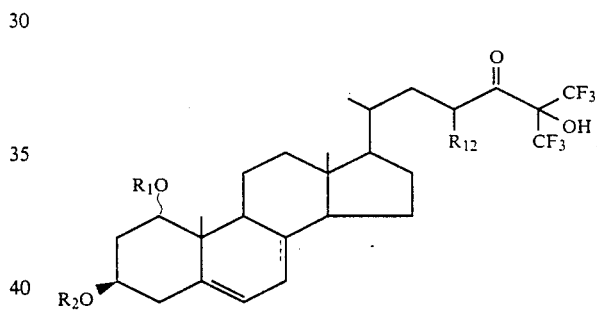

wherein $R_1$ and $R_2$ each denotes a hydrogen atom or a protecting group; $R_{12}$ denotes a halogen atom, alkanesulfonyloxy group or arenesulfonyloxy group; and the dotted line . . . between the carbon atoms of the 7- and the 8-position signifies the optional presence of a bond, which comprises oxidizing a compound represented by the formula

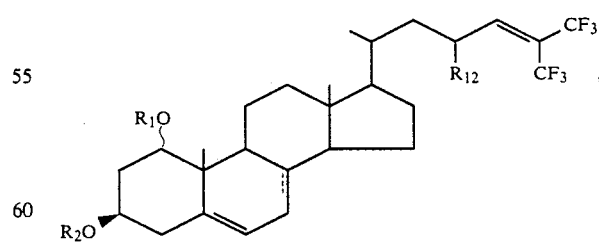

wherein $R_1$, $R_2$, $R_{13}$ and the dotted line . . . are as defined above, with a permanganate in the presence of an acid.

13. A compound represented by the general formula

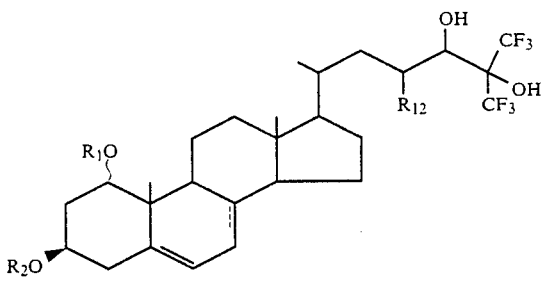

wherein $R_1$, $R_2$, $R_{12}$ and the dotted line . . . between the carbon atoms of the 7- and the 8-position are the same as defined in claim 12.

14. A process for producing a compound represented by the formula

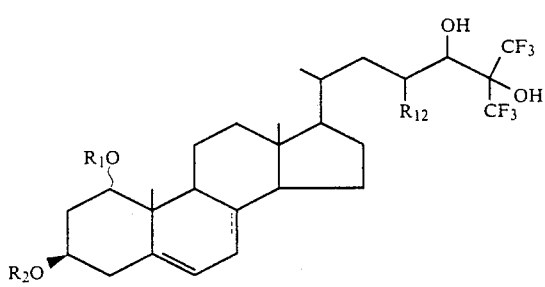

wherein $R_1$ and $R_2$ each denotes a hydrogen atom or a protecting group; $R_{12}$ denotes a halogen atom, alkanesulfonyloxy group, arensulfonyloxy group, hydroxyl group or protected hydroxyl group; and the dotted line . . . between the carbon atoms of the 7- and the 8-position signifies the optional presence of a bond, which comprises oxidizing a compound represented by the formula

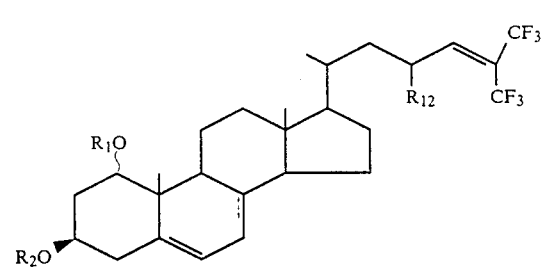

wherein $R_1$, $R_2$, $R_{12}$ and the dotted line . . . are as defined above, in the presence of a base.

15. A compound represented by the formula

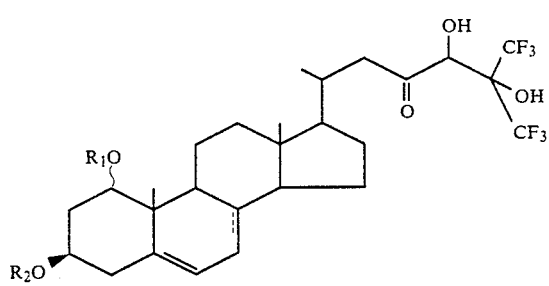

wherein $R_1$ and $R_2$ each denotes a hydrogen atom or a protecting group and the dotted line . . . between the carbon atoms of the 7- and the 8-position signifies the optional presence of a bond.

16. A process for producing a compound represented by the formula

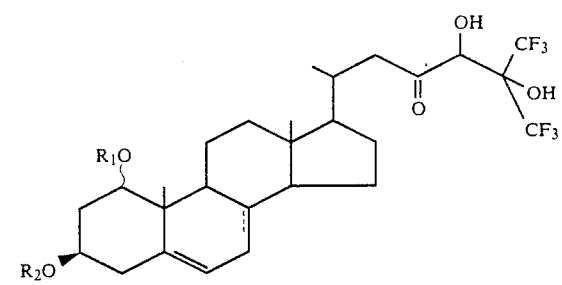

wherein $R_1$ and $R_2$ each denotes a hydrogen atom or a protecting group and the dotted line . . . between the carbon atoms of the 7- and 8-position signifies the optional presence of a bond, which comprises subjecting a compound represented by the general formula

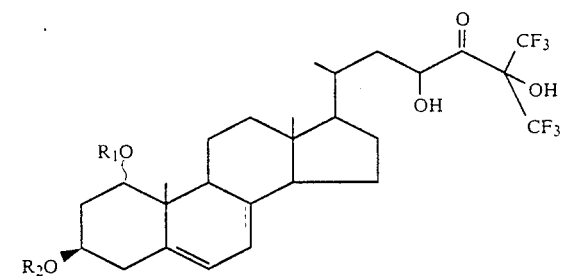

wherein $R_1$, $R_2$ and the dotted line . . . are as defined above, to heating in the presence of a tertiary amine.

17. A compound represented by the formula

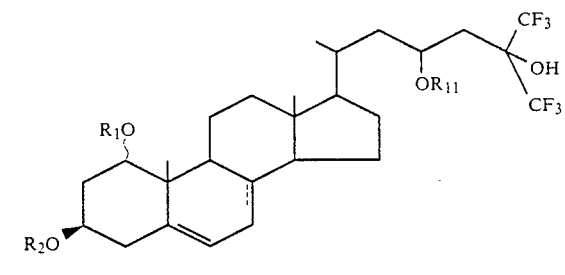

wherein $R_1$, $R_2$ and $R_{11}$ each denotes a hydrogen atom or a protecting group, and the dotted line . . . between the carbon atoms of the 7- and the 8-position signifies the optional presence of a bond.

18. A process for producing a compound represented by the formula

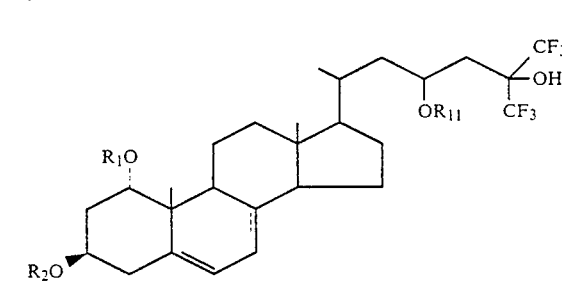

wherein $R_1$, $R_2$ and $R_{11}$ each denotes a hydrogen atom or a protecting group, and the dotted line . . . between the carbon atoms of the 7- and the 8-position signifies the optional presence of a bond, which comprises reacting a compound represented by the formula

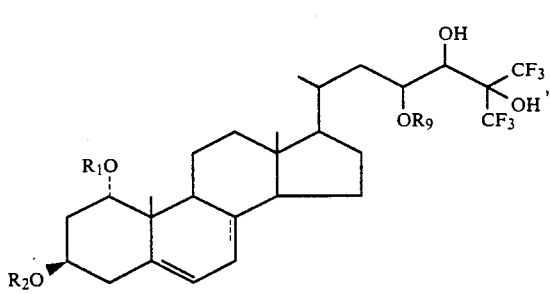

wherein $R_1$, $R_2$ and the dotted line . . . are as defined above, and $R_9$ denotes a protecting group, with an alkanesulfonyl halide or arenesulfonyl halide in the presence of a base to form a compound represented by the formula

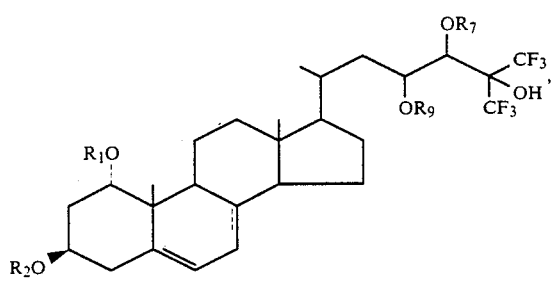

wherein $R_1$, $R_2$, $R_9$ and the dotted line . . . are as defined above, and $R_7$ denotes an alkanesulfonyl group or arenesulfonyl group, then treating the compound with a base to form an epoxy derivative represented by the formula

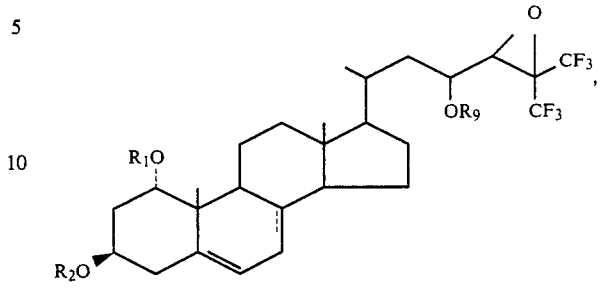

wherein $R_1$, $R_2$, $R_9$ and the dotted line . . . are as defined above, reducing the epoxy derivative and optionally subjecting the reduced product to deprotection reaction.

19. A pharmaceutical composition useful as a curative agent for diseases caused by disorders of absorption, transportation or metabolism of calcium, cell differentiation-inducing agent, antirheumatic agent or antipsosic agent which comprises as an active ingredient a pharmacologically effective amount of a compound of claim 2 and a carrier component.

20. A method of inducing cell differentiation which comprises administering an effective amount of a compound of claim 2 to a patient.

21. A method of treating diseases caused by disorders of absorption, transportation or metabolism of calcium, rheumatism or psoriasis which comprises administering an effective amount of a compound of claim 2 to a patient.

* * * * *